United States Patent
Knauf et al.

(10) Patent No.: US 6,348,642 B1
(45) Date of Patent: *Feb. 19, 2002

(54) RICINUS COMMUNIS β-KETOACYL-ACP SYNTHASE NUCLEIC ACIDS

(75) Inventors: Vic C. Knauf, Winters; Gregory A. Thompson, Davis, both of CA (US)

(73) Assignee: Calgene, LLC

( * ) Notice: Subject to any disclaimer, the term of this patent is extended or adjusted under 35 U.S.C. 154(b) by 0 days.

This patent is subject to a terminal disclaimer.

(21) Appl. No.: 07/987,256

(22) Filed: Dec. 7, 1992

Related U.S. Application Data

(63) Continuation of application No. 07/568,493, filed on Aug. 15, 1990.

(51) Int. Cl.⁷ ............................. A01N 5/00; C12N 5/14; C12N 15/82
(52) U.S. Cl. .................... 800/298; 435/320.1; 435/419; 536/23.2; 536/23.6
(58) Field of Search .......................... 435/172.3, 240.4, 435/320.1, 419, 468; 530/377; 800/205, DIG. 23, DIG. 69, 298; 536/23.2, 23.6, 24.5

(56) References Cited

U.S. PATENT DOCUMENTS

| | | | |
|---|---|---|---|
| 4,394,443 A | * | 7/1983 | Weissman et al. ............. 435/6 |
| 4,675,285 A | * | 6/1987 | Clark et al. .................... 435/6 |

FOREIGN PATENT DOCUMENTS

| | | | |
|---|---|---|---|
| EP | 0255377 | * 2/1988 | ........... C12N/15/00 |

OTHER PUBLICATIONS

McCabe et al 1988 Bio/Technology 6:923–926.*
Bubeck et al 1989 (Jun.) Crap Sci 29:652–656.*
Knauf 1987 Trends in Biotech 5:40–47.*
Battey et al 1989 (May) Trends in Biotech 7:122–126.*
Garwin et al., "Structural, Enzymatic, and Genetic Studies of β–Ketoacyl–Acyl Carrier Protein Synthases I and II of *Escherichia coli*," *J. Biol. Chem.* (1980) 255:11949–11956.
Schuz et al., "Partial Purification of β–Ketoacyl–Acyl Carrier Protein Synthase from a Higher Plant," *FEBS Letters* (1982) 140:207–209.
Shimikata and Stumpf, "Fatty Acid Synthetase of *Spinacia oleracea* Leaves," *Plant Physiol.* (1982) 69:1257–1262.
Shimikata and Stumpf, "Isolation and Function of Spinach Leaf β–Ketoacyl–[Acyl–Carrier–Protein] Synthases," *Proc. Nat. Acad. Sci.* (1982) 79:5808–5812.
Shimikata and Stumpf, "Purification and Characterization of β–Ketoacyl–ACP Synthetase I from *Spinacia oleracea* Leaves," *Arch. Biochem. Biophys.* (1983) 220:39–45.
Mohamed et al., "Primary Structure of the Mulitfunctional α Subunit Protein of Yeast Fatty Acid Synthase Derived from FAS2 Gene Sequence," *J. Biol. Chem.* (1988) 263:12315–21325.
Siggaard–Andersen, "Role of *Escherichia coli* β–Ketoacyl–ACP Synthase I in Unsaturated Fatty Acid Synthesis," *Carlsberg Res. Commun.* (1988) 53:371–379.
Kauppinen et al., "β–Ketoacyl–ACP Synthase I of *Escherichia coli*: Nucleotide Sequence on the fabB Gene and Identification of the Cerulenin Binding Residue," *Carlsberg Res. Commun.* (1988) 53:357–370.
Jaworski et al., "A Cerulenin Insensitive Short Chain 3–Ketoacyl–Acyl Carrier Protein Synthase in *Spinacia oleracea* Leaves," *Plant Physiol.* (1989) 90:41–44.
Bibb et al., "Analysis of the Nucleotide Sequence of the *Streptomyces glaucescens* tcmI Genes Provides Key Information About the Enzymology of Polyketide Antibiotic Biosynthesis," *EMBO J.* (1989) 8:2727–2736.
MacKintosh et al., "A New Assay Procedure to Study the Induction of β–Ketoacyl–ACP Synthase I and II, and the Complete Purification of β–Ketoacyl–ACP Synthase I from Developing Seeds of Oilseed Rape (*Brassica napus*)," *Biochem. Biophys. Acta* (1989) 1002:114–124.
Siggard–Andersen, "Purification and Characterization of a β–Ketoacyl–ACP Synthase from Barley Chloroplasts," *The Ninth International Symposium on Plant Lipids* (1990) Plant Lipid Biochemistry —Structure, Utilisation and Function, Abstract 53.
Kauppinen, "Molecular Cloning of the Gene(s) Coding for Barley β–Ketoacyl–ACP Synthase," *The Ninth International Symposium on Plant Lipids* (1990) Plant Lipid Biochemistry —Structure, Utilisation and Function, Abstract 66.
Clough et al., "Characterization of 3–Ketoacyl–ACP Synthase III from Spinach," *The Ninth International Symposium on Plant Lipids* (1990) Plant Lipid Biochemistry—Structure, Utilisation and Function, Abstract 64.

* cited by examiner

*Primary Examiner*—Amy J. Nelson

(57) ABSTRACT

By this invention, compositions and methods of use of *Ricinus communis* cDNAs encoding β-ketoacyl-ACP synthase, are provided. Also of interest are plants, plant parts and plant cells comprising the nucleic acid sequences.

15 Claims, 19 Drawing Sheets

F1: NTTISAPKKR

F2: VVITGTGLVSVFGNxVDTY

F3: LLAGESTIGLID

F4: GFNSQG$_W^Y$IDGK

F5: YxIVAGK

F6: ALEHADLGGDK

F7: AGVLVGTGMGGLTVFSDGVQALIxK

F8: ALSQR

F9: NDDPQTASR

F10: DGFVMGEGAGVLVMESL

F11: GAPIIAEYLGGAVNCDAYxMTDP

F12: ADGLGVSSCIER

F13: SLEDAGVSPEEVNYINAHATSTLAGDLAEIN

FIGURE 2

KR1:   SFSTDGWVAPK

KR2:   EEVNYINAxTSTPAGDL

KR3:   VFNDAIEALR

KR4:   DGFVMGEGAGVLLL

KR7:   VVVTGMGVVxPL

KR8:   SMIGxLLGAAGAVEAIATIEAI

KR10:  GGVxPNINLENPEEGV

KR11:  xGVxKEEVNYINAxATxTPAG

KR12:  xxPNINLENPEEGV

NT: KHPLMKQRRVVVTGMxV

FIGURE 3

Partial Amino
Acid Sequences        KR4                                              KR16
From 50 kD
Peptides      N   D   D   P   Q   T   A           E   E   V   N   Y   I   N   A AAT GAT GAT CCN CAA ACN GC|N        GAA GAA GTN AAT TAT ATT AAT GC|N
                  C   C       G                       G   G   C   C   C   C   C
                                                                              A Forward Primers 5'GACAAGCTT AAQ GAQ GAQ CCQ CAP ACN GC3'             652-2
5'GACAAGCTT AAQ GAQ GAQ CCP CAP ACN GC3'             652-3

Reverse Primers
                                                    (complements)

665-3     3'CTQ CTQ CAN TTP ATP TAP TTP CG CTTAAGCAG

FIGURE 4

```
1    GGCTTCTCTCCCAATTCATCGTTTGGATCGCTACCACTTCCGCCACCACCATGCAAGCCCTGC                          69
                                                          METGlnAlaLeuG
     PstI
     ─

70   AGTCCCCGTCTCTCCGACCATCCCCTCTAACCCCGCTCCATAAAATACTCACAATGCAGCAAAACGCC                     138
     lnSerProSerProLeuArgProSerProLeuThrProLeuHisLysAsnThrHisAsnAlaAlaLysArgP

139  CAACTAAAAAGGTCTCCTTTATCACCGATCATCAACAATAACAACGACGATTCAGCTCCAAAGC                          207
     roThrLysLysValSerPheIleThrAspHisGlnGlnGlnGlnArgArgPheSerLeuGlnSerA
     roThrLysLysValSerPheIleThrAspHisGlnGlnGlnGlnArgArgPheSerLeuGlnSerA

Note: Line 139 reads: CAACTAAAAAGGTCTCCTTTATCACCGATCATCAACAATAACAACGACGATTCAGCTCCAAAGC
      roThrLysLysValSerPheIleThrAspHisGlnGlnGlnGlnArgArgPheSerLeuGlnSerA 208  GAGAGAAAGACCCCAGAAAAAGGGTAGTCATAACTGGTACGGGTTTGGTATCTGTGTTTGGAATGATG                     276
     rgGluLysAspProArgLysArgValValIleThrGlyThrGlyLeuValSerValPheGlyAsnAspV 277  TCGATACTTACTACGATAAATTGCTTGCTGGAGAAGTGGGATCGGACTTATTGATAGGTTCGATGCGT                     345
     alAspThrTyrTyrAspLysLeuLeuAlaGlyGluSerGlyIleLeuIleAspArgPheAspAlaS 346  CTAAGTTCCTACTAGATTTGGTGGACAGATCAGGGGGTTTAATTCACTTGGTTATATTGATGGGAAAA                     414
     erLysPheProThrArgPheGlyGlyGlnIleArgGlyPheAsnSerLeuGlyTyrIleAspGlyLysA
                                                                    SphI
                                                                    ─

415  ATGATAGAAGGCTTGATGATTGTTTGAGGTATTGCATTGTTCTGGTAAAAAGCTCTTGTCGTAAAAAGCTCTTGAGCATGCTG       483
     snAspArgArgLeuAspAspCysLeuArgTyrCysIleValAlaAlaGlyLysLysAlaLeuGluHisAlaA

484  ATCTTGGTGGTGATAAGTTGTCTAAGATTGATAAAGAGCGAGCTGGTGTGCTTGTTGGAACAGGATGG                     552
     spLeuGlyGlyAspLysLeuSerLysIleAspLysGluArgAlaGlyValLeuValGlyThrGlyMETG
```

FIGURE 5A

553 GTGGTCTTACAGTCTTTTCAGATGGTGTTCAGGCCCTAATTGAAAAGGACACAGGAAAATTACCCCAT 621
    lyGlyLeuThrValPheSerAspGlyValGlnAlaLeuIleGluLysGlyHisArgLysIleThrProP

622 TCTTTATTCCTTATGCTATAACAAACATGGATCTGCCTTGTTAGCTATTGAACTTGGTCTCATGGGTC 690
    hePheIleProTyrAlaIleThrAsnMETGlySerAlaLeuLeuAlaIleGluLeuGlyLeuMETGlyP

691 CTAATTATTCAATTTCAACTGCTTGTGCTACCTCCAATTATTGCTTCTATGCTGCCAATCATATTC 759
    roAsnTyrSerIleSerThrAlaCysAlaThrSerAsnTyrCysPheTyrAlaAlaAlaAsnHisIleA

760 GCAGAGGTGAGGCTGAATTGATGATTGCTGGTGGAACTGAAGCCGCCATCATTCCAATCGGTTTGGGAG 828
    rgArgGlyGluAlaGluLeuMETIleAlaGlyThrGluAlaAlaIleIleProIleGlyLeuGlyG
                                                                NcoI

829 GTTTTGTAGCATGTAGGGCCTTATCACAAAGGAATGATGATCCACAAACTGCCTCAAGGCCATGGACA 897
    lyPheValAlaCysArgAlaLeuSerGlnArgAsnAspAspProGlnThrAlaSerArgProTrpAspL

898 AAGATCGAGATGGCTTTGTTATGGGTGAAGGTGCTGGAGTGTTGGTAATGGAGAGTTTGGAACATGCAA 966
    ysAspArgAspGlyPheValMETGlyGluGlyAlaGlyValLeuValMETGluSerLeuGluHisAlaM
                                                        ScaI

967 TGAAAAGGGGTGCACCAATAATTGCTGAGTACTTGGGAGGTGCTGTTAATTGTGATGCTTATCACATGA 1035
    ETLysArgGlyAlaProIleIleAlaGluTyrLeuGlyGlyAlaValAsnCysAspAlaTyrHisMETT
                                    997

FIGURE 5B

1036 CTGATCCAAGGGCTGATGGACTTGGGGTCTCTTCCTGCATTGAGAGAAGTCTTGAAGATGCCGGTGT 1104
     hrAspProGlnGlyLeuMetAspLeuGlyValSerSerCysIleGluSerLeuGluAspAlaGlyVals
                                    HpaI 1105 CACCTGAGGAGGTTAACTATATAAATGCACATGCAACTTCCACTCTTGCTGGTGACCTTNCTGAGATAA 1173
     erProGluGluValAsnTyrIleAsnAlaHisAlaThrSerThrLeuAlaGlyAspLeu    GluIleA
                                                          1119

1174 ATGCTATTAAAAAAGTATTCAAGAATACGTCTGACATCAAATCAATGCAAACCAAGTCTATGATAGGAC 1242
     snAlaIleLysLysValPheLysAsnThrSerAspIleLysIleAsnAlaThrLysSerMETIleGlyH

1243 ATTGCCTTGGTGCTGCTGGAGGTCTGGAAGCAATTGCCTGTGTGAAGGCCATTACCACAGGATGGTTGC 1311
     isCysLeuGlyAlaAlaGlyGlyLeuGluAlaIleAlaCysValLysAlaIleThrThrGlyTrpLeuH

1312 ATCCTACAATTAATCAATTTAACCCAGAGCCATCAGTTGAATTTGACACTGTTGCCAATAAGAAGCAGC 1380
     isProThrIleAsnGlnPheAsnProGluProSerValGluPheAspThrValAlaAsnLysLysGlnG

1381 AGCACGAAGTGAATGTTGCCATTTCAAATTCCTTTGGATTCGGTGGACACAACTCTGTGGTAGCCTTTT 1449
     lnHisGluValAsnValAlaIleSerAsnSerPheGlyPheGlyGlyHisAsnSerValValAlaPheS

NcoI

1450 CTGCATTTAAACCCTGAGAGCATGGTTTCTTCTGCATTCGGGCCGCGGTCATTTACATTACCATGGC 1518
     erAlaPheLysPro

FIGURE 5C

1519 CTGCATTTCTTGTAGGAACCACTGGAGAGTTGCTTGCTTATAGACAGAGTCATCGACATCACTTCCCCC 1587
1588 TTTTAGCTTTTTGAGCTGCTGATAGTAGTCAGTTTCTCATTTCAGTATCAAGTCTATCTTAAGAAGGTC 1656
1657 TTGCTTATTTTCTTT 1672

FIGURE 5D

```
              140       150       160       170       180       190
     AGKKALEHADLGGDKLSKIDKERAGVLVGTGMGGLTVFSDGVQA-LIEKGHRKITPFF
134  ||  ||   |   |    ||     ||| ||      | ||   |  ||  |
 76  FLSMEQAIADAGLSPEAYQNNPRVGLIAGSGGGSPRFQVFGADAMRGPRGLKAVGPYV
              80        90        100       110       120       130

200       210       220       230       240
     IPYAITNMGSALLAIELGLMGPNYSISTACATSNYCFYAAANHIRRGEAELMIAGGTE
     | || |   |   | ||||| |||||| |||| ||  |       ||   |||
     VTKAMASGVSACLATPFKIHGVNYSISSACATSAHCIGNAVEQIQLGKQDIVFAGGGE
              140       150       160       170       180       190

250       260       270       280       290       300
     AAIIPIGLGGFVACRALS-QRNDDPQTASRPWDKDRDGFVMGEGAGVLVMESLEHAMK
     |  || |  ||       |  |    |    | || |||  || |||  |  || |
     -ELCWEMACEFDAMGALSTKYNDTPEKASRTYDAHRDGFVIAGGGGMVVVEELEHALA
              200       210       220       230       240

310       320       330       340       350       360
     RGAPIIAEYLGGAVNCDAYHMTDPRADGLGVSSCIERSLEDAGVSPEEVNYINAHATS
     |||  || | |||  |  |   |        |         |||||||| |||  |
     RGAHIYAEIVGYGATSDGADMVAPSGEGAVRCMKMAMHGVD----TPIDYLNSHGTS
              260       270       280       290       300

370       380       390
     TLAGDLXEINAIKKVFKNTSDIKINATKSMIGH    396
     | || | || | | || ||  |    |  | ||
     TPVGDVKELAAIREVFGDKS-PAISATKAMTGH    333
              310       320       330
```

FIGURE 6A

```
                140        150        160        170        180        190
134   VDHTLAVEQLFDYFVPTSICREVAWEAGAEGPVTVVSTGCTSGLDAVGYGTELIRDGR
       ||          ||                                    ||
181   KGHRKITPFFIPYAITNMGSALLAIELGLMGPNYSISTACATSNYCFYAAANHIRRGE
                190        200        210        220        230

200        210        220        230        240
      ADVVVCGATDAPISPITVACFDAIKATSANNDDPAHASRPFDRNRDGFVLGEGSAVFV
      | ||         ||||    ||| |   |||  ||||||||| ||||||||||||
      AELMIAGGTEAAIIPIGLGGFVACRALSQRNDDPQTASRPWDKDRDGFVMGEGAGVLV
240        250        260        270        280        290

250        260        270        280        290        300
LEELSAARRRGAHAYAEVRGFATRSNAFHMTGLKPDGREMAEAITAALDQARRTGDDL
||||                |||||||||||||||||| |||||  ||||
MESLEHAMKRGAPIIAEYLGGAVNCDAYHMTDPRADGLGVSSCIERSLEDAGVSPEEV
     300        310        320        330        340        350

310        320        330        340        350        360
HYINAHGSGTRQNDRHETAAFKRSLGQRAYDVPVSSIKSMIGHSLGAIGSLELAACAL
|||||                              ||||||||| || ||| |||||
NYINAHATSTLAGDLXEINAIK-KVFKNTSDIKINATKSMIGHCLGAAGGLEAIACVK
     360        370        380        390        400        410

370        380        390        400        410        420
AIEHGVIPPTANYEEPDPECDLDYVPNVAREQRVDTVLSVGSGFGGFQSAAVLARPK         422
||                                 ||  ||| |||||
AITTGWLHPTINQFNPEPSVEFDTVANKKQQHEVNVAISNSFGFGGHNSVVAFSAFK         468
     420        430        440        450        460
```

FIGURE 6B

```
  1 ATGATTACCTGAAAATAAGTATAATTTGTATTGAAATTATAAAGTGACATTTTTTGTGTAACAAATATT          69
 70 TTGTGTAACAAGAATTAAAAAAAACAGAAAATACTCAGCTTTTTTAATAATAAAAAAATTAATTG            138
139 AGTTAGAAATTGTTGTACCAATAACAAAAGATTTATATGGAATTATAAATCAACACACCAATAACAC          207
208 AAGACTTTTTAAAAATTTAAGAATAATATAAGCAATAACAATAGAATCTTCAAATTCTTCAAATTCCTTA       276
277 AAAATCAATCTCCCACTATTAATCCCCCTAGTTTTAGTTGGTAATGGCAACGTTTGTTGACTACCGTA         345
346 TTGTAACTTTTGTCAAATTGTCATAAATACGTGTCAAACTCTGGTAAAAAATTAGTCTGCTACATCTGT        414
415 CTTTTATTATTATAAAACACAGCTGTTAATCAGAATTTGGTTTATTAAATCAACAACCTGCACGAAACTTG      483
484 TGTGAGCATATTTGTCTGTTCTGGTTCATGACCTTCTCCGCATGATGGCCAAGTGTAATGGCCACT           552
                                                                  BglII
                                                                  |
553 TGCAAGAGCGTTCTTCAACGAGAGTAAGTCGAACAAATATTTGTCCGTTACGACCACATATAANATCTC        621
                                                   616
622 CCCATCTCTATATATAATACCAGCATTCACCATCATGAATACCTCCAAATCTCCAATCTCACAAATACTTC      690
691 AATAAAAAGACCAAAAATTAAAGCAAAGAAAAGCCTTCTTGTGCACAAAAAAAAGAAGCCTTCT             759
760 AGGTTTTCACGACATGAAGTTCACTACTCTAATGGTCATCACATTGGTGATAATCGCCATCTCGTCTCC        828
                METLysPheThrThrLeuMETValIleThrLeuValIleIleAlaIleSerPr
829 TGTTCCAATTAGAGCAACCACGGTTGAAAGTTTCGGAGAAGTTGGCACAATCGTGTGTTGACAGAACT         897
    oValProIleArgAlaThrThrValGluSerPheGlyGluValAlaGlnSerCysValValThrGluLe
```

FIGURE 7A

```
 898  CGCCCCATGCTTACCAGCAATGACCACCGGCAGGAGACCCGACTACAGAATGCTGCGACAAACTGGTAGA   966
      uAlaProCysLeuProAlaMETThrThrAlaGlyAspProThrThrGluCysCysAspLysLeuValGl

967  GCAGAAACCATGTCTTTGTGGTTATATTCGAAACCCAGCCTATAGTATGTATGTTACTTCTCCAAACGG  1035
      uGlnLysProCysLeuCysGlyTyrIleArgAsnProAlaTyrSerMETTyrValThrSerProAsnGl

1036  TCGCAAAGTCTTAGATTTTTGTAAGGTTCCTTTTCCTAGTGTTGTTAAATCTCTCAAGACATTGCTAAGAA  1104
      yArgLysValLeuAspPheCysLysValProPheCysLysProSerCys
                                               BglII                    HindII
                                                |                         |
1105  AAATATTATTAAAAAATAAAAGAATCAAACTAGATGTAACAATGAATCATCATGTTATGGTTGAA  1173
                                              1136                        1173

1174  GCTTATATAGCTGAAGTGTTTTTGATTTTATATATGTGTGTGTCCTGCTCAATTTTTGAAACAC  1242

1243  ACACGTTTCTCCCTGATTTGGATTTAAATTATATTTGAGTAAAAAAAGAAAAAGATGGAATGCTATT  1311
                                              EcoRV
                                                |
1312  TATACAAGTTGATGAAAAAGTGGAAGTACAATTTAGATATCTCCWWCACTTAAAGAATGAAACAATAAT  1380
                                              1350
                                                                  SalI
                                                                    |
1381  AGACTTCGAAACAAATGAAAAATACATAAATTGTCGACAATCAACGTCGATCGACGAGTTTATTATTAA  1449
                                                  1414

1450  AAATTTGTGTGAAGGACTAGCAGTTCAACCAAATGATATTGAACATATACATCAACAAATATGATAATC  1518
```

FIGURE 7B

```
1519  ATAAAGAGAGAATGGGGGGGTGTCGTTTACCAGAAACCCTCTTTTTCTCAGCTCGCTAAAACCCTA  1587
1588  CCACTAGAGACCTAGCTCTGACCGTCGGCTCATCGGTGCCGGAGGTGTAACCTTTCTTTCCCATGACCC  1656
1657  GAAACCCTCTCTTTCCCAACTCACGAAAACCTACAATCAAAAACCTAGCTCCGACCATCGGCTCATCGG  1725
                                                            ClaI
                                                            |
1726  TGCCGAAGGTGTAACCTTTCNCTCCCATCATAGTTTCTCGTAAATGAAAGCTAATTGGGCAATCGATTT  1794
                                                1789
1795  TTTAATGTTTAAACCATGCCAAGCCATTCTTATAGGACAATTGTCAATAATAGCATCTTTGAGTTTT  1863
1864  GTCTCAAAAGTGACACTAGAAGAAAAAGTCACAAAAATGACATTCATTAAAAGTAAAATATCCCTAA  1932
1933  TACCTTTGGTTTAAATTAAATAAGTAAACAAAAATAAAATAAAACAAATAAAATAAAATAAAAATGA  2001
2002  AAAAAGAAATTTTTTTTATAGTTTCAGATTATATGTTTCAGATTCGAAATTTTTAAA  2060
```

FIGURE 7C

```
                                                                        HindIII
                                                                          |
  1  GCTCACTTGTGTGGTGGAGGAGAAAAACAGAACTCACAAAAAGCTTTGCGACTGCCAAGAACAACAACA        69
                                                  42

70  ACAACAAGATCAAGAGAAGAAGAAGAAGAAGATCAAAAATGGCTCTTCGAATCACTCCAGTGACCTTGCAA     138
                                        METAlaLeuArgIleThrProValThrLeuGln

EcoRV                                    BglII          NcoI
            |                                        |              |
139  TCGGAGAGATATCGTTCGTTTCGTTTCCTAAGAAGGCTAATCTCCCAGATCTCCCAAATTCGCCATGGCC     207
     SerGluArgTyrArgSerPheSerPheProLysLysAlaAsnLeuArgSerProLysPheAlaMETAla
            149                                      185             201

HindII
                                                           |
208  TCCACCCTCGGATCATCCACACCGAAGGTTGACAATGCCAAGAAGCCTTTCAACCTCCACGAGAGGTT      276
     SerThrLeuGlySerSerThrProLysValAspAsnAlaLysLysProPheGlnProProArgGluVal
                                       238

277  CATGTTCAGGTGACGCACTCCATGCCACCACAGAAGATTTCAAATCCATGAGGTTGGGCT             345
     HisValGlnValThrHisSerMETProProGlnLysIleLeuIlePheLysSerIleGluGlyTrpAla

346  GAGCAGAACATATTGGTTCACCTAAAGCCAGTGGAGAAATGTTGGCAAGCACAGGATTCTTGCCGGAC     414
     GluGlnAsnIleLeuValHisLeuLysProValGluLysCysTrpGlnAlaGlnAspPheLeuProAsp

415  CCTGCATCTGAAGGATTTGATGAACAAGTCAAGGAACTAAGGCAAGAGCAAAGGAGATTCCTGATGAT     483
     ProAlaSerGluGlyPheAspGluGlnValLysGluLeuArgGlnValLysGluLeuArgAlaArgAlaAlaLysGluIleProAspAsp
```

FIGURE 8A

484 TACTTTGTTGTTTGGTTGGAGATATGATTACAGAGGAAGCCCTACCTACTTACCAAACAATGCTTAAT  552
    TyrPheValValLeuValGlyAspMETIleThrGluAlaLeuProThrTyrGlnThrMETLeuAsn

553 ACCCTAGAGATGGTGTACGTGATGAGACTGGGGCTAGCCTTACGCCTTGGGCTGTCTGGACTAGGCTTGG  621
    ThrLeuAspGlyValArgAspGluThrGlyAlaSerLeuThrProTrpAlaValTrpThrArgAlaTrp

PvuII                                              AccI
                     —                                                  —
622 ACAGCTGAAGAGAACAGGCATGGCGATCTTCCACACCTATCTCTACCTTTCTGGGGGTAGACATG  690
    ThrAlaGluGluAsnArgHisGlyAspLeuLeuHisThrTyrLeuTyrLeuSerGlyArgValAspMET
    626                                                              684

BamHI
                                                —
691 AGGCAGATACAGAAGACAATTCAGTATCTCATTGGGTCAGGAATGGATCCTCGTACCGAAAACAGCCCC  759
    ArgGlnIleGlnLysThrIleGlnTyrLeuIleGlySerGlyMETAspProArgThrGluAsnSerPro
                                                                    736

760 TACCTTGGGTTCATCTACACATCGTTTCAAGAGCGTGCCACATTGTTTCTCACGGAAACACCGCCAGG  828
    TyrLeuGlyPheIleTyrThrSerPheGlnArgAlaThrPheValSerHisGlyAsnThrAlaArg

SphI
                 —
829 CATGCAAAGGATCATGGGACGTGAAACTGGCCGCAAATTTGTGGTACAATCGCGTCTGACGAAAAGCGT  897
    HisAlaLysAspHisGlyAspValLysLeuAlaGlnIleCysGlyThrIleAlaSerAspGluLysArg
    833

FIGURE 8B

```
                                                    ClaI
                                                    |
 898  CACGAGACCGCTTATACAAAGATCGAAAAGCTATTCGAGATCGATCCTGATGGCACCGTTCTTGCT   966
      HisGluThrAlaTyrThrLysIleValGluLysLeuPheGluIleAspProAspGlyThrValLeuAla
                                                    942

BglII
                       |
 967  TTTGCCGACATGATGAGGAAAAGATCTCGATGCCCGCACACTTGATGTACGATGGGCGTGATGACAAC  1035
      PheAlaAspMETMETArgLysIleSerMETProAlaHisLeuMETTyrAspGlyArgAspAspAsn
                       990

AccI
                                                 |
1036  CTCTTCGAACATTTCTCGGCGGTTGCCCAAAGACTCTACACCGCCAAAGACTACGCCGACATA  1104
      LeuPheGluHisPheSerAlaValAlaGlnArgLeuLeuArgLeuValTyrThrAlaLysAspTyrAlaAspIle
                                                 1077

1105  CTGGAATTTCTGGTCGGGCGGTGGAAAGTGGCGGATTTGACCGGCCTATCTGGTGAAGGGCGTAAAGCG  1173
      LeuGluPheLeuValGlyArgTrpLysValAlaAspLeuThrGlyLeuSerGlyGluGlyArgLysAla

SacI
                                                    |
1174  CAAGATTATGTTTGCGGGTTGCCACCAAGAATCAGAAGGCTGGAGGAGAGAGCTCAAGGGCGAGCAAAG  1242
      GlnAspTyrValCysGlyLeuProProArgIleArgArgLeuGluArgAlaGlnGlyArgAlaLys
                                                    1228
```

FIGURE 8C

```
                   PvuII
                   ─

1243  GAAGGACCTGTTGTTCCATTCAGCTGGATTTTCGATAGACAGGTGAAGCTGTGAAGAAAAAAAACGA  1311
      GluGlyProValValProPheSerTrpIlePheAspArgGlnValLysLeu
                                        1266

1312  GCAGTGAGTTCGGTTTCTGTTGGCTTATTGGGTAGAGGTTAAAACCTATTTTAGATGTCTGTTTCGTGT  1380

1381  AATGTGGTTTTTTTTCTTCTAATCTTGAATCTGGTATTGTGTCGTTGAGTTCGCGTGTGTAAACTTG  1449

1450  TGTGGCTGTGGACATATTATAGAACTCGTTATGCCAATTTTGATGACGGTGGTTATCGTCTCCCCTGGT  1518

1519  GTTTTTTTATTGTTT  1533
```

FIGURE 8D

1 TGAGAGATAGTGTGAGAGCATTAGCCTTAGAGAGAGAGAGAGAGCTTGTGTCTGAAAGAATCCACAA 69

HindIII
   |
70 ATGGCATTGAAGCTTAACCCTTTGGCATCTCAGCCTTACAACTTCCCT 117
   METAlaLeuLysLeuAsnProLeuAlaSerGlnProTyrAsnPhePro

FIGURE 9A

```
                              PstI
                               |
  1  ACTTCATGGGCTATTTGGACAAGAGCTTGGACTGCAGAAGAGAACCGACACGGTGATCTTCTCAATAAG  69
     ThrSerTrpAlaIleTrpThrArgAlaLeuTrpThrArgArgThrAlaGluAsnArgHisGlyAspLeuLeuAsnLys

70  TATCTTTACTTGTCTGGACGTGTTGACATGAGGCAGATTGAAAAGACCATTCAGTACTTGATTGGTTCT 138
     TyrLeuTyrLeuSerGlyArgValAspMETArgGlnIleGluLysThrIleGlnTyrLeuIleGlySer

BamHI
                   |
139  GGAATGGATCCTAGAACAGAGAACAATCCTTACCTCGG 176
     GlyMETAspProArgThrGluAsnAsnProTyrLeuAla
```

RICINUS COMMUNIS β-KETOACYL-ACP SYNTHASE NUCLEIC ACIDS

This is a continuation of application Ser. No. 07/568,493, filed Aug. 15, 1990.

FIELD OF INVENTION

The present invention is directed to synthase enzymes relevant to fatty acid synthesis in plants, protein preparations, amino acid and nucleic acid sequences related thereto, and methods of use for such compositions.

INTRODUCTION

BACKGROUND

Plant oils are used in a variety of industrial and edible uses. Novel vegetable oils compositions and/or improved means to obtain oils compositions, from biosynthetic or natural plant sources, are needed. Depending upon the intended oil use, various different fatty acid compositions are desired.

For example, in some instances having an oilseed with a higher ratio of oil to seed meal would be useful to obtain a desired oil at lower cost. This would be typical of a high value oil product. In some instances, having an oilseed with a lower ratio of oil to seed meal would be useful to lower caloric content. In other uses, edible plant oils with a higher percentage of unsaturated fatty acids are desired for cardiovascular health reasons. And alternatively, temperate substitutes for high saturate tropical oils such as palm and coconut, would also find uses in a variety of industrial and food applications.

One means postulated to obtain such oils and/or modified fatty acid compositions is through the genetic engineering of plants. However, in order to genetically engineer plants one must have in place the means to transfer genetic material to the plant in a stable and heritable manner. Additionally, one must have nucleic acid sequences capable of producing the desired phenotypic result, regulatory regions capable of directing the correct application of such sequences, and the like. Moreover, it should be appreciated that in order to produce a desired phenotype requires that the Fatty Acid Synthetase (FAS) pathway of the plant is modified to the extent that the ratios of reactants are modulated or changed.

Higher plants appear to synthesize fatty acids via a common metabolic pathway. In developing seeds, where fatty acids attached to triglycerides are stored as a source of energy for further germination, the FAS pathway is located in the proplastids. The first step is the formation of acetyl-ACP (acyl carrier protein) from acety-CoA and ACP catalyzed by the enzyme, acetyl-CoA:ACP transacylase (ATA). Elongation of acetyl-ACP to 16- and 18- carbon fatty acids involves the cyclical action of the following sequence of reactions: condensation with a two-carbon unit from malonyl-ACP to form a β-ketoacyl-ACP (β-ketoayl-ACP synthase), reduction of the keto-function to an alcohol (β-keyoayl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). Common plant unsaturated fatty acids, such as oleic, linoleic and α-linolenic acids found in storage triglycerides, originate from the desaturation of stearoyl-ACP to form oleoyl-ACP (C18:1) in a reaction catalyzed by a soluble plastid Δ-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound Δ-12 desaturase and Δ-15 desaturase. These "desaturases" thus create mono- or polyunsaturated fatty acids respectively.

A third β-keyoayl-ACP synthase has been reported in *S. oleracea* leaves having activity specific toward very short acyl-ACPs. This acetoacyl-ACP synthase or "β-ketoacyl-ACP" synthase III has a preference to acetyl-CoA over acetyl-ACP, Jaworski, J. G., et al., *Plant Phys.* (1989) 90:41–44. It has been postulated that this enzyme may be an alternate pathway to begin FAS, instead of ATA.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful plant sources for nucleic acid sequences of such enzyme targets capable of modifying fatty acid compositions are needed. Ideally an enzyme target will be amenable to one or more applications alone or in combination with other nucleic acid sequences, relating to increased/decreased oil production, the ratio of saturated to unsaturated fatty acids in the fatty acid pool, and/or to novel oils compositions as a result of the modifications to the fatty acid pool. Once enzyme target(s) are identified and qualified, quantities of protein and purification protocols are needed for sequencing. Ultimately, useful nucleic acid constructs having the necessary elements to provide a phenotypic modification and plants containing such constructs are needed.

BRIEF DESCRIPTION OF THE FIGURES

FIG. 2 provides partial amino acid sequence of peptides from the *R. communis* 50 kD β-ketoacyl ACP synthase protein listed in order found in cDNA clone. Each fragment represents amino acid sequence obtained from an HPLC purified fraction resulting from digestion of the 50 kD protein with trypsin or endoproteinase gluC. F1 shows amino terminal protein sequence obtained from the undigested 50 kD protein. A lower case x represents a sequence cycle where it was not possible to identify the amino acid residue. The positions with two amino acids represents sequences of two nearly identical peptides with a clear difference in sequence at the indicated position, suggesting microheterogeneity of the 50 kD protein.

FIG. 3 provides partial amino acid sequence of peptides from the *R. communis* 46 kD β-ketoacyl ACP synthase protein. Each fragment labeled with a KR represents amino acid sequence obtained from an HPLC purified fraction resulting from digestion of the 46 kD protein with trypsin. Amino terminal protein sequence obtained from the undigested 46 kD protein is also shown (NT). "x" is as defined in FIG. 2.

FIG. 4 provides the oligonucleotide primers used in PCR from the *R. communis* β-ketoacyl-ACP synthase 50 kD peptides KR4 and KR16. Primers are shown in one orientation only. Oligonucleotides in both orientations were used as the order of peptides KR4 and KR16 in the synthase protein was not known.

FIG. 5 provides preliminary cDNA sequence and the corresponding translational peptide sequence derived from the cDNA clone, pCGN2765, which encodes the 50 kD synthase protein. The cDNA includes both the plastid transit peptide sequence (amino acids 1–42) and the sequence encoding the mature protein.

FIG. 6A shows protein sequence homology of the translated amino acid sequence of the 50 kD clone with the FabB synthase gene from *E. coli*. The top line is translated amino acid sequence from the cDNA encoding the 50 kD synthase protein and the bottom line is translated amino acid sequence of the *E. coli* synthase encoded by FabB.

FIG. 6B shows protein sequence homology of the translated amino acid sequence of the 50 kD clone with "ORF-1" of the polyketide synthesis gene from Streptomyces. The top line is ORF-1 translated amino acid sequence and the bottom line is translated amino acid sequence from the cDNA encoding the 50 kD synthase protein.

FIG. 7 provides approximately 2 kb of genomic sequence of Bce4.

FIG. 8 provides a cDNA sequence and the corresponding translational peptide sequence derived from *C. tinctorius* desaturase. The cDNA includes both the plastid transit peptide sequence (amino acids 1–33) and the sequence encoding the mature protein.

FIG. 9A represents preliminary partial DNA sequence of a 1.6 kb *Brassica campestris* desaturase cDNA clone, pCGN3235, from the 5' end of the clone.

FIG. 9B represents preliminary partial DNA sequence of a 1.2 kb *Brassica campestris* desaturase cDNA clone, pCGN3236, from the 5' end of the clone. Initial sequence from the 3' ends of the two *Brassica campestris* desaturase clones, indicates that pCGN3236 is a shorter clone from the same gene as pCGN3235.

SUMMARY OF THE INVENTION

Figure 1:
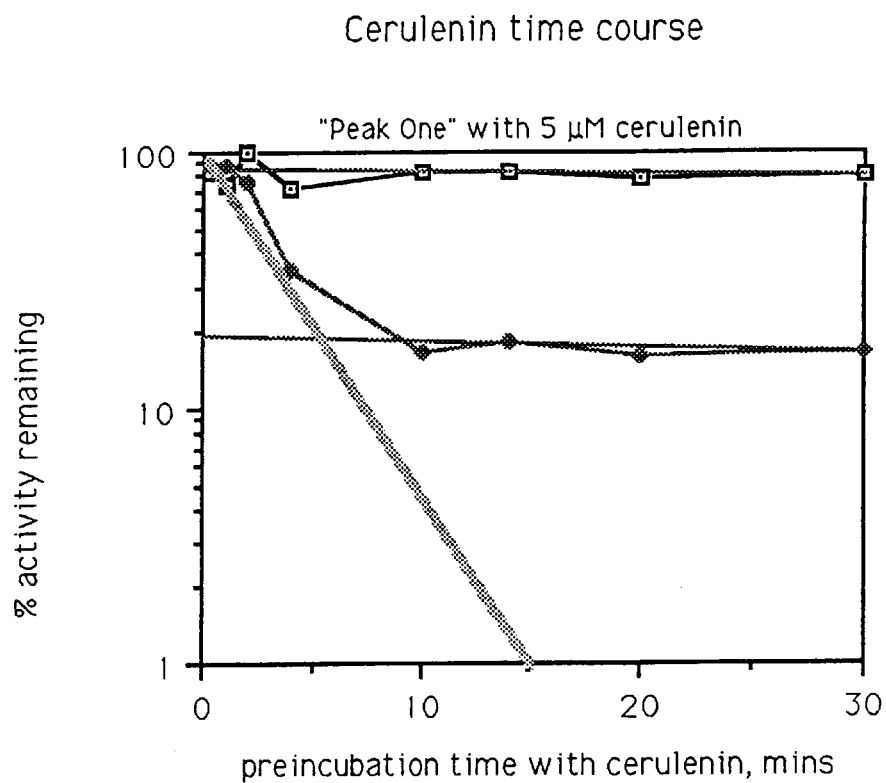
FIG. 1 shows the time course of inactivation of synthase activities in the first peak of synthase activity from ACP-affinity chromatography by 5 $\mu$M cerulenin. At the outset of the experiment, the activity with C16:0-ACP is approximately twice that with C10:0-ACP, indicating an enrichment for type-II synthase in the sample. The graph shows that activity with C16:0-ACP, representing type-II synthase is virtually insensitive to cerulenin, while activity with C10:0-ACP is inhibited by greater than 80% after 10 minutes. The remaining activity with C10:0-ACP is probably low activity of type-II synthase in the sample with the C10:0-ACP substrate (approximately 10% of the activity with C16:0-ACP); this means that type-I synthase is completely inactivated at this cerulenin concentration by 15 min. (heavy dotted line).

By this invention, compositions and methods of use related to β-keyoayl-ACP synthase, hereinafter also referred to as "synthase", are provided. Also of interest are methods and compositions of amino acid and nucleic acid sequences related to biologically active plant synthase(s).

In particular, synthase protein preparations which have relatively high turnover (specific activity) are of interest for use in a variety of applications, in vitro and in vivo. Especially, protein preparations having synthase I and/or synthase II activities are contemplated hereunder. Synthase activities are distinguished by the preferential activity towards longer and shorter acyl-ACPs. Protein preparations having preferential activity towards shorter chain length acyl-ACPs are synthase I-type. Synthases having preferential activity towards longer chain length acyl-ACPs are synthase II-type. Of special interest are synthases obtainable from *Ricinus communis*.

Nucleic acid sequences encoding a synthase biologically active in a host cell may be employed in nucleic acid constructs to modulate the amount of synthase present in the host cell, especially the relative amounts of synthase I-type and synthase II-type proteins when the host cell is a plant host cell. A synthase may be produced in host cells for harvest or as a means of effecting a contact between the synthase and its substrate. Host cells include prokaryotes and/or eukaryotes. Plant host cells containing recombinant constructs encoding a synthase, as well as plants and cells containing modified levels of synthase protein(s) are also provided.

By this invention, methods of catalyzing the condensation reaction between an acyl-ACP having a chain length of $C_2$ to $C_{16}$ and malonyl-ACP is effected by contacting an acyl-ACP and malonyl-ACP substrates with a synthase obtainable from *R. communis* under conditions which permit the condensation of the reactants. Although the reaction employs a *R. communis* synthase, this reaction may occur outside of a *R. communis* cell. Using various techniques, this reaction can be conducted in vitro or in other plant cell hosts in vivo. For example, one may grow a plant cell having integrated in its genome an expression construct having, in the 5' to 3' direction of transcription, a plant expressible promoter, a DNA sequence encoding a synthase obtainable from *R. communis* and a transcription termination region. Of interest is the modulation of synthases alone and in conjunction with each other. For expression in plants, the use of promoters capable of preferentially directing transcription and translation in embryo tissue to regulate the expression of a synthase may be desired.

In addition, nucleic acid constructs may be designed to decrease expression of endogenous synthase in a plant cell as well. One example is the use of an anti-sense synthase sequence under the control of a promoter capable of expression in at least those plant cells which normally produce the enzyme.

Additionally, one may wish to coordinate expression of a synthase with the expression of other introduced sequences encoding other enzymes related to fatty acid synthesis, for example plant thioesterases, especially medium-chain thioesterases, desaturases, especially Δ-9 desaturases, and the like. When nucleic acid constructs encoding such factors are prepared for introduction into a plant cell, the transcriptional initiation regions will most likely be different from each other.

Synthase preparations obtained from *R. communis*, substantially free of protein contaminants are described. *R. communis* synthase preparations may be obtained which demonstrate synthase I-type activity and those which demonstrate synthase II-type activity. Enzyme specific activities of up to 16 μmol/min/mg protein and 1.7 μmol/min/mg protein have been observed for synthase I type and synthase II-type protein preparations, respectively. Proteins or protein preparations displaying such activities, alone or in combination, may be contacted with fatty acid synthesis substrates to drive synthase condensation reactions. The amino acid and nucleic acid sequences corresponding to the various preparations may be deduced and used to obtain other homologously related synthases.

DETAILED DESCRIPTION OF THE INVENTION

A plant synthase of this invention includes any sequence of amino acids, polypeptide, peptide fragment or other protein preparation, whether derived in whole or in part from natural or synthetic sources which demonstrates the ability to catalyze a condensation reaction between an acyl-ACP or acyl-CoA having a chain length of $C_2$ to $C_{16}$ and malonyl-ACP in a plant host cell. A plant synthase will be capable of catalyzing a synthase reaction in a plant host cell, i.e., in vivo, or in a plant cell-like environment, i.e., in vitro. Typically, a plant synthase will be derived in whole or in part from a natural plant source.

Synthase I demonstrates preferential activity towards acyl-ACPs having shorter carbon chains, $C_2$–$C_{14}$; synthase II demonstrates preferential activity towards acyl-ACPs having longer carbon chains, $C_{14}$–$C_{16}$. Synthase III demonstrates preferential activity towards acyl-CoAs having very short carbon chains, $C_2$ to $C_6$. Other plant synthases may also find applicability by this invention, including synthase III type activities. Differences between synthases I, II, and III are also observed in inhibition with cerulenin. Synthase I is most sensitive, synthase II less sensitive and synthase III the least sensitive to cerulenin. In FIG. 1, a time course assay of cerulenin effects on synthase I and synthase II activities is provided. It can be seen from these results, that synthase II has some synthase I-type activities.

Synthases include modified amino acid sequences, such as sequences which have been mutated, truncated, increased and the like, as well as such sequences which are partially or wholly artificially synthesized. Synthases and nucleic acid sequences encoding synthases may be obtained by partial or homogenous purification of plant extracts, protein modeling, nucleic acid probes, antibody preparations, or sequence comparisons, for example. Once purified synthase is obtained, it may be used to obtain other plant synthases by contacting an antibody specific to *R. communis* synthase with a plant synthase under conditions conducive to the formation of an antigen:antibody immunocomplex and the recovery of plant synthase which reacts thereto. Once the nucleic acid sequence encoding a synthase is obtained, it may be employed in probes for further screening or used in genetic engineering constructs for transcription or transcription and translation in host cells, especially plant host cells.

Recombinant constructs containing a nucleic acid sequence encoding a synthase and a heterologous nucleic acid sequence of interest may be prepared. By heterologous is meant any sequence which is not naturally found joined to the synthase sequence. Hence, by definition, a sequence joined to any modified synthase is not a wild-type sequence. Other examples include a synthase sequence from one plant source which is integrated into the genome of a different plant host.

Constructs may be designed to produce synthase in either prokaryotic or eukaryotic cells. The increased expression of a synthase in a plant cell or decreased amount of endogenous synthase observed in a plant cell are of special interest. Moreover, in a nucleic acid construct for integration into a plant host genome, the synthase may be found in a "sense" or "anti-sense" orientation in relation to the direction of transcription. Thus, nucleic acids may encode biologically active synthases or sequences complementary to the sequence encoding a synthase to inhibit the production of endogenous plant synthase. By transcribing and translating a sense sequence in a plant host cell, the amount of synthase available to the plant FAS complex is increased. By transcribing or transcribing and translating an anti-sense sequence in a plant host cell, the amount of the synthase available to the plant FAS is decreased. Ideally, the anti-sense sequence is very highly homologous to the endogenous sequence. Other manners of decreasing the amount of synthase available to FAS may be employed, such as ribozymes or the screening of plant cells transformed with constructs containing sense sequences which in fact act to decrease synthase expression, within the scope of this invention. Other analogous methods may be applied by those of ordinary skill in the art.

Synthases may be used, alone or in combination, to catalyze the elongating condensation reactions of fatty acid synthesis depending upon the desired result. For example, rate influencing synthase activity may reside in synthase I-type, synthase II-type, synthase III-type or in a combination of these enzymes.

Thus, over-expression of synthase I could serve to increase fatty acid yield, and/or the proportion of palmitic acids (C16:0) found in the system. Alternatively, as a critical enzyme in several fatty acid elongation steps, reducing endogenous synthase I might effectively provide low yields of fatty acids. As the last enzyme in the fatty acid elongation pathway, synthase II may be a critical factor to increase production of fatty acids. Increased availability of synthase II to FAS may in effect "drive" the rate of reaction forward and result in a larger pool of long chain fatty acids. In turn, the presence of an increased amount of fatty acids with 18 carbons may result ultimately, in the increased production of triglycerides. In a like manner, the decrease of synthase II may work to decrease one or both of these mechanisms. Because synthase II catalyzes final elongation steps, it may require support from other synthase factors to create the desired effect. In particular, the combined presence of synthase I and synthase II are contemplated for the generation of a high composition of oleic fatty acids and/or increased triglyceride production. In addition, the production of palmitate may be further enhanced by a combination of increased synthase I production and reduction in endogeous synthase II. Thus, various synthase factors may be combined in a like fashion to achieve desired effects.

Other applications for use of cells or plants producing synthase may also be found. For example, potential herbicidal agents selective for plant synthase may be obtained through screening to ultimately provide environmentally safe herbicide products. Especially in that bacterial systems do not have an enzyme equivalent to plant synthase II, they may be particularly useful systems for the screening of such synthase II based herbicides. The synthase can also be used in conjunction with chloroplast lysates to enhance the production and/or modify the composition of the fatty acids prepared in vitro. The synthase can also be used for studying the mechanism of fatty acid formation in plants and bacteria. For these applications, constitutive promoters may find the best use.

Constructs which contain elements to provide the transcription and translation of a nucleic acid sequence of interest in a host cell are "expression cassettes". Depending upon the host, the regulatory regions will vary, including regions from structural genes from viruses, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli*, *B. subtilis*, *Saccharomyces cerevisiae*, including genes such as β-galactosidase, T7 polymerase, trp-lac (tac), trp E and the like.

An expression cassette for expression of synthase in a plant cell will include, in the 5' to 3' direction of transcription, a transcription and translation initiation control regulatory region (also known as a "promoter") functional in a plant cell, a nucleic acid sequence encoding a synthase, and a transcription termination region. Numerous transcription initiation regions are available which provide for a wide variety of constitutive or regulatable, e.g., inducible, transcription of the desaturase structural gene. Among transcriptional initiation regions used for plants are such regions associated with cauliflower mosaic viruses (35S, 19S), and structural genes such as for nopaline synthase or mannopine synthase or napin and ACP promoters, etc. The transcription/translation initiation regions corresponding to such structural genes are found immediately 5' upstream to the respective start codons. Thus, depending upon the intended use, different promoters may be desired.

Of special interest in this invention are the use of promoters which are capable of preferentially expressing the synthase in seed tissue, in particular, at early stages of seed oil formation. Selective modification of seed fatty acid/oils composition will reduce potential adverse effects to other plant tissues. Examples of such seed-specific promoters include the region immediately 5' upstream of a napin or seed ACP genes such as described in co-pending U.S. Ser. No. 147,781, desaturase genes such as described in co-pending U.S. Ser. No. 494,106, or Bce-4 gene such as described in co-pending U.S. Ser. No. 494,722. Alternatively, the use of the 5' regulatory region associated with the plant synthase structural gene, i.e., the region immediately 5' upstream to a plant synthase structural gene and/or the transcription termination regions found immediately 3' downstream to the plant synthase structural gene, may often be desired. In general, promoters will be selected based upon their expression profile which may change given the particular application.

Sequences found in an anti-sense orientation may be found in cassettes which at least provide for transcription of the sequence encoding the synthase. By anti-sense is meant a DNA sequence in the 5' to 3' direction of transcription which encodes a sequence complementary to the sequence of interest. It is preferred that an "anti-sense synthase" be complementary to a plant synthase gene indigenous to the plant host. Any promoter capable of expression in a plant host which causes initiation of high levels of transcription in all storage tissues during seed development is sufficient. Seed specific promoters may be desired.

In addition, one may choose to provide for the transcription or transcription and translation of one or more other sequences of interest in concert with the expression or anti-sense of the synthase sequence, for example sequences encoding a plant desaturase such as described in co-pending U.S. Ser. No. 494,106 and U.S. Ser. No. unassigned, filed on or about Aug. 13, 1990 entitled "Plant Desaturases—Compositions and Use", seed or leaf acyl carrier protein such as described in co-pending U.S. Ser. No. 437,764, medium-chain plant thioesterase such as described in co-pending U.S. Ser. No. 514,030, or other sequence encoding an enzyme capable of affecting plant lipids, to affect alterations in the amounts and/or composition of plant oils. The general methods of use and means to determine related sequences and compositions described above as to synthase enzymes may be applied to these enzymes as well.

One may wish to integrate nucleic acids encoding a desaturase sense sequence and synthase sense sequence into the genome of a host cell. A plant desaturase includes any enzyme capable of catalyzing the insertion of a first double band into a fatty acid-ACP moiety, especially $\Delta$-9 desaturase. Such a combination may be designed to modify the production of unsaturated fatty acids and thus either lead to significantly lower or higher saturated fat upon the expression of both enzymes in a plant host cell. As desaturase acts upon the longer chain fatty acyl-ACPs, the resulting product of synthase II activity, various applications are possible. Of interest is the combination of an enhanced production of both synthase II and $\Delta$-9 desaturase for the production of fatty acids having little or no completely saturated chains. It may also be of interest to provide for the increased production of synthase II and a decreased production of desaturase for the production of high stearate (C18:0) fatty acid compositions. The modified pool of saturated/unsaturated fatty acids may be reflected in the composition of resulting triglycerides. In a different embodiment, it may be desired to combine the increased expression of a synthase, such as synthase I, with a medium-chain plant thioesterase. Plants containing a medium-chain plant thioesterase, an enzyme capable of having preferential hydrolase activity toward one or more medium-chain (C8 to C14) acyl-ACP substrates, are contemplated for the production of medium chain fatty acids, especially laurate (C12:0). In combination with an increased level of one or more synthases, these effects may be augmented.

When one wishes to provide a plant transformed for the combined effect of more than one nucleic acid sequence of interest, typically a separate nucleic acid construct will be provided for each. The constructs, as described above contain transcriptional or transcriptional and translational regulatory control regions. One skilled in the art will be able to determine regulatory sequences to provide for a desired timing and tissue specificity appropriate to the final product in accord with the above principles set forth as to synthase expression or anti-sense constructs. When two or more constructs are to be employed, whether they are both related to synthase sequences or a synthase sequence and a sequence encoding an enzyme capable of affecting plant lipids, it is desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

Of special interest are synthases which appear to have superior kinetic properties, isolated from protein preparations obtainable from plants such as *Prunus amygdalus,* or more preferred *Ricinus communis.* As shown in Table I, in comparison of crude extracts from *Spinacia oleracea* leaf and some plants with low levels of saturated oils, *R. communis* and *P. amygdalus* show a markedly higher total activity of synthase II activity per gram fresh weight; calculated specific activities are also higher.

TABLE I

Synthase II yields and substrate Km values in crude extracts from various sources[1]

| Source Tissue | Protein mg/g Fr Wt | Activity mU/g Fr Wt | Specific Activity mU/mg Protein | Km (C16-ACP) μM |
|---|---|---|---|---|
| S. oleracea Leaf | 7.15 | 6.61 | 0.962 | 14.0 |
| B. napus Seed | 7.62 | 6.58 | 0.864 | 22.0 |
| R. communis Endosperm | 21.0 | 346.0 | 16.5 | 15.7 |
| P. amygdalus Embryo | 8.07 | 62.3 | 7.73 | 22.4 |

[1]S. oleracea leaf extract was prepared according to Shimakata & Stumpf, PNAS 79:5808–5812 (1983). The remaining samples were prepared from ground tissue which had been mixed with two volumes of buffer (2 mg/g fresh meal weight) containing 50 mM potassium phosphate and 2 mM dithiothreitol, pH 7.5, of which the supernatant fluid was collected after centrifugation. Protein was assayed by the Bradford method. (Analy. Biochem. (1976) 72:248–254) Synthase II was assayed as described in Example 2 and with the palmitoyl-ACP in varying concentrations.

Tests also compared the sensitivity of the crude extracts to substrate concentration. It was assumed that malonyl-ACP would be proportional to added ACP due to the presence of malonyl transacylase in the crude extracts. The results showed very little differences in $K_m$ for palmitoyl-ACP or in sensitivity to ACP/malonyl-ACP between species. Other analogous plant sources may be determined by similar testing.

The exceptionally low level of saturated fat (<1%) and high activity of the synthase II enzyme in crude extracts are qualities which indicate R. communis as exemplary of a preferred enzyme source. Of special interest is R. communis seed produced by a primary inflourescence or flower spike, as it usually has a higher oil content and higher synthase II specific activity, than the seed of branches from a secondary or tertiary inflourescence (secondary spikes). A major difficulty with the R. communis tissue is the toxicity of the R. communis seed storage ricins. Ricin is removed from the extract during the purification of the synthases as discussed in more detail below. Also, the stage at which the seeds are harvested influences the amount of ricin present in the tissue.

"Early" seeds have a very small central opaque core, a predominant translucent tissue, and very low levels of protein and synthase II activity. "Prime" seed tissue, which is found at about 21–28 days after flower opening have a central opaque white core, which contains the deposited seed oil and ricin, surrounded by a translucent white tissue. The seed coat is just beginning to harden and turn from white to a purplish-brown. The translucent tissue gradually disappears and the opaque core increases during maturation. As shown in Table II, the "Prime" tissue from the primary flower spikes have the highest synthase II specific activity; these are a main source of synthase II. The more mature "Late" seeds continue to exhibit high synthase II activity, but the large increase in deposition of ricin dilutes the specific activity. With improved methods of removing ricin, the older seeds may prove to be preferred sources as well.

TABLE II

β-Ketoacyl-ACP Synthase II Activity in Developing Seeds on Primary and Secondary Flower Spikes of R. communis[1]

| Sample | Specific Activity (μUnits/mg protein) |
|---|---|
| A | 936 ± 39 |
| B | 2615 ± 139 |
| C | 10364 ± 544 |
| D | 9537 ± 1342 |
| E | 8386 ± 261 |
| F | 5034 ± 171 |
| G | 1735 ± 134 |
| H | 1459 ± 4 |
| I | 4936 ± 87 |
| J | 3466 ± 30 |
| K | 6115 ± 193 |

[1]Individual R. communis seeds were identified as Early (A,B,G,H), Prime (C,D,I) or Late (E,F,J,K). Seeds A–F were from primary spikes and seeds G–K were from secondary spikes. Each endosperm tissue from seed was ground in two volumes (ml/g fresh weight) of 40 mM potassium phosphate, 20% glycerol (v/v), 1 mM sodium EDTA, 2 mM DTT, pH 7.5, with a pestle in a microcentrifuge tube. The homogenate was clarified by centrifugation at 11,600 × g for 15 minutes. The supernatant was assayed for protein by the Bradford method (Analy. Biochem. (1976) 72:248–254) and for synthase II activity as described in Example 2.

As demonstrated more fully in the Examples, extraction and purification of synthases I and II from R. communis is obtained by ammonium sulfate fractionation (pH 7.5) and then subjecting the supernatant fluid to saturation with ammonium sulfate to precipitate the synthases. The pellet containing synthase activity is resuspended and the activity is bound to Reactive Green-19 Agarose. A column containing the activity bound to the Green-19 Agarose is prepared and the synthase activity is eluted in a high salt wash. The protein associated with fractions of peak activity is partially desalted and then absorbed to an ACP-Sepharose column and eluted with a gradient of 100–250 mM potassium phosphate buffer. The ACP column removes several proteins including a major contaminant which also showed a molecular weight at about 50 kD. Fractions assayed for synthase activity show that a major peak having primarily synthase II-type, but also containing some synthase I-type, activity elutes first and that fractions eluting after the major peak contain primarily synthase I-type activity.

When applied to SDS-PAGE analysis, fractions from the major peak having synthase II activity are shown to contain two major bands, one at about 46 kD and a second at about 50 kD. Synthase II activity has not been observed separate from protein preparations containing both the 50 kD and a 46 kD band. The relationship between the 50 and 46 kD bands is under further investigation, including cerulinin assays and E. coli expression studies. Two-dimensional gel analysis separates the 50 kD band into at least two spots.

Fractions eluting after the major peak contain mainly synthase I-type activity and show one distinctive band at about 50 kD. Tests with monoclonal antibodies indicate that the 50 kD proteins from the two fractions are very similar. Additional work is underway to further characterize these proteins biochemically.

Given the few bands provided in the SDS-PAGE, immediate efforts to obtain the corresponding amino acid and/or nucleic acid sequences thereto are possible in accordance with methods familiar to those skilled in the art. From such sequences, synthase activity may be further confirmed with expression in controlled systems, such as E. coli, or by observation of effects of transcription of anti-sense nucleic acid fragments and the like.

Amino acid sequences of fragments corresponding to purified protein preparations may be obtained through digestion with a protease, such as trypsin, and sequencing of resulting peptide fragments. Amino acid sequences of peptide fragments derived from the 50 kD protein are shown in FIG. 2 and from the 46 kD protein in FIG. 3 (FIG. 4 shows peptide sequences of the 50 kD peptide used to design oligonucleotide by "reverse translation" of peptide fragment amino acid sequences). DNA sequences are chosen for use in Polymerase Chain Reactions (PCR) using *R. communis* endosperm cDNA as a template to obtain longer DNA sequences. FIG. 4 is a DNA sequence corresponding to the 50 kD protein obtained by PCR. The resulting PCR-generated sequences are then used as labeled probes in screening a *R. communis* endosperm cDNA or genomic DNA library. In this manner, the full length clones corresponding to the *R. communis* proteins seen on the SDS-PAGE may be obtained if desired. Other plant synthase genes may be obtained by screening of cDNA or genomic libraries from other plant sources with probes derived from the synthase cDNA.

In FIGS. 6A and 6B we present sequence comparison between the translated amino acid sequence from an isolated cDNA clone which encodes the 50 kD synthase protein and two other known synthase proteins. Comparison to FabB, the gene encoding β-ketoacyl-ACP synthase I in *E. coli.* in FIG. 6A, indicates there is extensive identical homology of amino acids, especially near the active site, amino acids 219–223 of the FabB protein. The 50 kD translated amino acid sequence also has significant identical homology to a polyketide synthase protein in *Streptomyces glaucescens* that is encoded by ORF-1, as shown in FIG. 6B. The polyketide synthase protein is homologous to other known synthases, especially at the active site.

A DNA sequence of this invention may include genomic or cDNA sequence. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" protein (or enzyme). As synthases are part of the FAS pathway of plastid organelles, such as the chloroplast, proplastid, etc., transit peptides may be required to direct the protein(s) to substrate. A transit peptide sequence from any plastid-translocating sources may be employed, such as from ACP especially seed ACP, small subunit of ribulose bisphosphate carboxylase (RuBC), plant desaturase or from the native sequence naturally associated with the respective synthase.

The complete genomic sequence of a plant synthase may be obtained by the screening of a genomic library with a probe and isolating those sequences which hybridize thereto as described more fully below. Regulatory sequences immediately 5', transcriptional and translational initiation regions, and 3', transcriptional and translational termination regions, to the synthase may be obtained and used with or without the synthase structural gene.

Other synthases and/or synthase nucleic sequences are obtainable from amino acid and DNA sequences provided herein. "Obtainable" refers to those plant synthases which have sufficiently similar sequence to that of the native sequence(s) of this invention to provide a biologically active synthase. One skilled in the art will readily recognize that antibody preparations, nucleic acid probes (DNA and RNA) and the like may be prepared and used to screen and recover synthases and/or synthase nucleic acid sequences from other sources. Thus, sequences which are homologously related to or derivations from either *R. communis* synthase I or II are considered obtainable from the present invention.

"Homologeously related" includes those nucleic acid sequences which are identical or conservatively substituted as compared to the native sequence. Typically, a homologously related nucleic acid sequence will show at least about 60% homology, and more preferably at least about 70% homology, between the *R. communis* synthase and the given plant synthase of interest, excluding any deletions which may be present. Homology is determined upon comparison of sequence information, nucleic acid or amino acid, or through hybridization reactions.

Probes can be considerably shorter than the entire sequence, but should be at least about 10, preferably at least about 15, more preferably at least 20 or so nucleotides in length. Longer oligonucleotides are also useful, up to the full length of the gene encoding the polypeptide of interest. Both DNA and RNA can be used.

A genomic library prepared from the plant source of interest may be probed with conserved sequences from a *R. communis* synthase cDNA to identify homologously related sequences. Use of an entire *R. communis* synthase cDNA may be employed if shorter probe sequences are not identified. Positive clones are then analyzed by restriction enzyme digestion and/or sequencing. In this general manner, one or more sequences may be identified providing both the coding region, as well as the transcriptional regulatory elements of the synthase gene from such plant source. cDNA libraries prepared from other plant sources of interest may be screened as well, providing the coding region of synthase genes from such plant soruces.

In use, probes are typically labeled in a detectable manner (for example with $^{32}P$-labeled or biotinylated nucleotides) and are incubated with single-stranded DNA or RNA from the plant source in which the gene is sought, although unlabeled oligonucleotides are also useful. Hybridization is detected, typically using nitrocellulose paper or nylon membranes by means of the label after single-stranded and double-stranded (hybridized) DNA or DNA/RNA have been separated. Hybridization techniques suitable for use with oligonucleotides are well known to those skilled in the art. Thus, plant synthase genes may be isolated by various techniques from any convenient plant. Plant genes for synthases from developing seed obtained from other oilseed plants, such as *C. tinctorius* seed, rapeseed, cotton, corn, soybean cotyledons, jojoba nuts, coconut, peanuts, oil palm and the like are desired as well as from non-traditional oil sources, such as *S. oleracea* chloroplast, avocado mesocarp, Cuphea, California Bay and *Euglena gracillis.* Synthases, especially synthase I, obtained from Cuphea may show specialized activities towards medium chain fatty acids. Such synthase may be of special interest for use in conjunction with a plant medium-chain thioesterase.

Once the desired plant synthase sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized, where one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like. For expression, the open reading frame coding for the plant synthase or functional fragment thereof will be joined at its 5' end to a transcriptional initiation regulatory control region. In some instances, such as modulation of plant synthase via a nucleic acid sequence encoding synthase in an anti-sense orientation, a transcription initiation region or transcription/translation initiation region may be used. In embodiments wherein the expression of the synthase protein is desired in a plant host, a transcription/translation initiation regulatory region, is needed. Additionally, modified promoters, i.e., having transcription initiation regions derived from one gene source and translation initiation regions derived from a different gene source or enhanced promoters, such as double 35S CaMV promoters, may be employed for some applications.

As described above, of particular interest are those 5' upstream non-coding regions which are obtained from genes regulated during seed maturation, particularly those preferentially expressed in plant embryo tissue, such as ACP- and napin-derived transcription initiation control regions. Such regulatory regions are active during lipid accumulation and therefore offer potential for greater control and/or effectiveness to modify the production of plant desaturase and/or modification of the fatty acid composition. Especially of interest are transcription initiation regions which are preferentially expressed in seed tissue, i.e., which are undetectable in other plant parts. For this purpose, the transcript initiation region of acyl carrier protein isolated from *B. campestris* seed and designated as "Bcg 4-4" and a gene having an unknown function isolated from *B. campestris* seed and designated as "Bce-4" are also of substantial interest.

Briefly, Bce4 is found in immature embyro tissue at least as early as 11 days after anthesis (flowering), peaking about 6 to 8 days later or 17–19 days post-anthesis, and becoming undetectable by 35 days post-anthesis. The timing of expression of the Bce4 gene closely follows that of lipid accumulation in seed tissue. Bce4 is primarily detected in seed embryo tissue and to a lesser extent found in the seed coat. Bce4 has not been detected in other plant tissues tested, root, stem and leaves.

Bce4 transcript initiation regions will contain at least 1 kb and more preferably about 5 to about 7.5 kb of sequence immediately 5' to the Bce4 structural gene.

The Bcg 4-4 ACP message presents a similar expression profile to that of Bce4 and, therefore, also corresponds to lipid accumulation in the seed tissue. Bcg 4-4 is not found in the seed coat and may show some differences in expression level, as compared to Bce4, when the Bcg 4-4 5' non-coding sequence is used to regulate transcription or transcription and translation of a plant Δ-9 desaturase of this invention.

The napin 1-2 message is found in early seed development and thus, also offers regulatory regions which can offer preferential transcriptional regulation of a desired DNA sequence of interest such as the plant desaturase DNA sequence of this invention during lipid accumulation. Napins are one of the two classes of storage proteins synthesized in developing Brassica embryos (Bhatty, et al., *Can J. Biochem.* (1968) 46:1191–1197) and have been used to direct tissue-specific expression when reintroduced into the Brassica genome (Radke, et al., *Theor. Appl. Genet.* (1988) 75:685–694).

As to regulatory transcript termination regions, these may be provided by the DNA sequence encoding the plant synthase or a convenient transcription termination region derived from a different gene source, especially the transcript termination region which is naturally associated with the transcript initiation region. Typically, the transcript termination region will contain at least about 1 kb, preferably about 3 kb of sequence 3' to the structural gene from which the termination region is derived.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformed cells. The gene may provide for resistance to a cytotoxic agent, e.g. antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

The manner in which the DNA construct is introduced into the plant host is not critical to this invention. Any method which provides for efficient transformation may be employed. Various methods for plant cell transformation include the use of Ti- or Ri-plasmids, microinjection, electroporation, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), either being permissible, so long as the vir genes are present in the transformed Agrobacterium host. The armed plasmid can give a mixture of normal plant cell and gall.

A preferred method for the use of Agrobacterium as the vehicle for transformation of plant cells employs a vector having a broad host range replication system, at least one T-DNA boundary and the DNA sequence or sequences of interest. Commonly used vectors include pRK2 or derivatives thereof. See, for example, Ditta et al., *PNAS USA*, (1980) 77:7347–7351 and EPA 0 120 515, which are incorporated herein by reference. Normally, the vector will be free of genes coding for opines, oncogenes and vir-genes. Included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

The vector is used for introducing the DNA of interest into a plant cell by transformation into an Agrobacterium having vir-genes functional for transferring T-DNA into a plant cell. The Agrobacterium containing the broad host range vector construct is then used to infect plant cells under appropriate conditions for transfer of the desired DNA into the plant host cell under conditions where replication and normal expression will occur. This will also usually include transfer of the marker, so that cells containing the desired DNA may be readily selected.

The expression constructs may be employed with a wide variety of plant life, particularly plant life involved in the production of vegetable oils. These plants include, but are not limited to rapeseed, peanut, sunflower, C. tinctorius, cotton, Cuphea, soybean, and corn or palm.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

In addition, synthase I or II produced in accordance with the subject invention can be used in preparing antibodies for assays for detecting plant synthases from other sources. The plant synthases can also be used in conjunction with chloroplast lysates to enhance the production and/or modify the composition of the fatty acids prepared in vitro. The plant synthase can also be used for studying the mechanism of fatty acid formation in plants and bacteria.

The invention now being generally described, it will be more readily understood by reference to the following examples which are included for purposes of illustration only and are not intended to limit the present invention.

EXAMPLES

Materials

Commercially available biological chemicals and chromatographic materials, including Reactive Green 19 agarose, Ponceau S, ammonium carbonate, sodium borohydride ($NaBH_4$), malonyl CoA, free fatty acids, β-mercaptoethanol, and protease inhibitors amino caproic acid, leupeptin, pepstatin, and phenylmethylsulfonyl fluoride are from Sigma (St. Louis, Mo.). CNBr-activated Sepharose 4B is purchased from Pharmacia (Piscataway, N.J.). Proteolytic enzymes, including trypsin and endoproteinase gluC, are sequencing grade enzymes obtained from Boehringer Mannheim Biochemicals (Indianapolis, Ind.). Polyvinylidenefluoride (PVDF) membranes are Immobilon-P (Millipore, Bedford, Mass.). HPLC grade acetonitrile, methanol, chloroform and water are obtained from Burdick and Jackson (Muskegon, Mich.). Organic solvents including glacial acetic acid and methanol are from J. T. Baker (Phillipsburg, N.J.). Tetrahydrofuran, dimethylphenylthiourea (DMPTU), and HPLC grade trifluoroacetic acid (TFA) are from Applied Biosystems (Foster City, Calif.); all chemicals utilyzed in the Applied Biosystems 477A Sequencer (see below) are also from Applied Biosystems (ABI). Radiochemicals, including $^{14}C$-malonyl-Coenzyme A, [9,10(n)-3H] oleic acid (10 mCi/mmol), and decanoic acid are from New England Nuclear (NEN (Dupont), Boston, Mass.). [3H]-iodoacetic acid is from Amersham, (Arlington Heights, Ill.).

Example 1

In this example, the effects of additions of paartially purified β-ketoacyl-ACP synthase and/or Δ-9 desaturase to FAS systems in cell-free extracts are described.

A. Synthase Experiment

1. Purification of S. oleracea Leaf Synthase II 1.1 Assay. Synthase II activity is detected radiometrically as described in Example 2.

1.2 Purification. β-ketoacyl-ACP synthase II is partially purified from S. oleracea leaf according to the protocol of Shimakata and Stumpf (PNAS (1982) 79:5808–5812), with the following changes.

The Sephacryl S300 (Pharmacia) column is 2.5 cm×100 cm and the flow rate is 18 ml/hour. Synthase I and II activities co-elute in a single peak.

The Affi-gel blue-agarose column (Bio-Rad, Richmond, Calif.) is 1.5 cm×14 cm and the flow rate is 10 ml/hour. The synthase II activity requires 300 mM phosphate for elution.

The Whatman (Clifton, N.J.) P11 cellulose phosphate column, 1.5 cm×14 cm, is run at 9 ml/hour. As phosphate at 50 mM potassium phosphate as was reported by Shimakata and Stumpf (supra), the phosphate salt concentration is reduced to 10 mM both in the column buffer and in the applied sample. The synthase I activity does not adsorb to the column even at 10 mM potassium phosphate and is recovered in the flow-through. The synthase II activity is eluted step-wise at 100 mM phosphate.

1.3 Specific Activity. One unit of activity is defined as the amount of protein required for the formation of 1 μmol of β-ketoacyl-ACP condensation product per minute. This is measured as incorporation of 1 μmole [2-$^{14}$C]malonate, supplied as [2-$^{14}$C]-malonyl-COA, into β-ketoacyl-ACP per minute at 37° C. under assay conditions. The recovery of synthase II activity was 164 mU from 30 g S. oleracea leaves, with a specific activity of 31.6 mU/mg protein. The recovery of activity was 35%. Protein is measured by the Bradford method (Analy. Biochem. (1976) 72:248–254).

2. Substrate Specificity

The partially purified S. oleracea leaf synthase II activity is twelve times more active with the palmitoyl-ACP substrate than with decanoyl-ACP. In order to show that the small amount of decanoyl-ACP activity observed is from synthase II, the activity is tested for sensitivity to cerulenin, an irreversible inhibitor of synthase I activity. Since the synthase I activity does not adsorb to the cellulose phosphate, the activity in the flow-through from that column is compared to the synthase II activity peak from cellulose phosphate. Each enzyme source is incubated with 5 μM cerulenin for 15 minutes at room temperature before being assayed with each of the acyl-ACP substrates. After incubation with cerulenin, the decanoyl-ACP activity is reduced 99% in the cellulose phosphate flow-through fraction and only 69% in the synthase II fraction. The palmitoyl-ACP activity in the synthase II fraction is not inhibited by the cerulenin treatment.

3. Preparation of Cell-free Extracts

Brassica napus is grown in the greenhouse under a 16-hour photoperiod with temperatures ranging from 76° F.(days) to 60° F. (nights). The seedpods are collected at 24–28 days after flowering. The seeds are removed from the pods, frozen in liquid nitrogen, and ground with a mortar and pestle. The powder is triturated with two volumes (2 ml/g fresh weight) of buffer containing 50 mM potassium phosphate, 2 mM dithiothreitol, pH 7.5. The sample is mixed by vortex for one minute and clarified by centrifugation at 10,000×g for 15 minutes. Soluble protein is measured by the Bradford method (supra.). A clarified homogenate is made from *S. oleracea* leaves according to the protocol of Shimakata and Stumpf (1982, supra.) through the step involving centrifugation at 10,000×g.

The extracts are assayed for endogenous β-ketoacyl-ACP synthase II activity as described in Example 2. The synthase II activity in the *S. oleracea* leaf extract was 228 μU/mg protein. The synthase II activity in the Brassica developing seed extract was 1200 μU/mg protein.

4. Fatty Acid Synthetase Reaction

The FAS reaction includes in a 250 μl volume 100 mM HEPES-NaOH buffer, pH 8.0, 2 mM dithiothreitol, 400 μM each NADH and NADPH, 10.4 μM ACP, 12 μM acetyl coenzyme A, 5 μM [2-14C]malonyl coenzyme A (NEN, specific activity 55 Ci/mol), 300 μg protein from *B. napus* seed or *S. oleracea* leaf cell-free extracts, and varying amounts of partially purified synthase II.

The partially purified synthase II from *S. oleracea* leaf is added to the *S. oleracea* leaf FAS reaction mix at 1-, 2-, and 10-fold excess, and to the Brassica seed FAS reaction mix at 0.2-, 0.4-, and 2-fold excess. The reactions are incubated for ten minutes at 33° C. and are stopped by the addition of 1 ml of hexane-isopropanol (3:2, v:v) and 667 μl sodium sulfate from a 6.67% (w/v) solution. The phases are mixed by vortex for 30 seconds and separated by centrifugation at 4,500×g for one minute. The hexane-isopropanol layer is removed by aspiration, and the sample is re-extracted. The hexane-isopropanol extracts are combined and an aliquot is counted in Aquasol (NEN) in a Beckman (Fullerton, Calif.) LS7800 liquid scintillation counter.

5. Detection

The hexane-isopropanol is evaporated from the extracts under a stream of nitrogen gas and the lipids are saponified in 200 μl methanol with 100 μM potassium hydroxide for thirty minutes at 80° C. The saponified lipids are cooled to room temperature and titrated to pH 8.5 with 1 N hydrochloric acid in methanol to a phenolphthalein endpoint. The methanol is evaporated under a stream of nitrogen gas. Phenacyl esters of the fatty acids in each sample are prepared by incubation with 100 μl p-Bromophenacyl-8 (Pierce, Rockford, Ill.) and 300 μl acetonitrile at 80° C. for 30 minutes. The sample is cooled to room temperature, 40 μl HPLC-grade water is added, and the solution is clarified by centrifugation at 4,500×g for five minutes. The supernatant fluid is injected on to an Ultrasphere ODS reverse-phase HPLC column (5 micron particle size, 4.6 mm×25 cm; Beckman, Fullerton, Calif.) equilibrated in 80% acetonitrile in water. The fatty acid phenacyl esters are eluted at one ml per minute in 80% acetonitrile in water for 10 min., followed by a one minute gradient of 80–100% acetonitrile in water, and finally, by 100% acetonitrile for 19 min. Elution of the esters is monitored by UV absorbance and by radioactivity.

In both the *S. oleracea* leaf and the Brassica developing seed extracts, with an increase in the amount of synthase II added to the FAS system, the percent of radioactivity in palmitic acid decreases with a corresponding increase in the radioactivity detectable in stearic acid. In the table below, the radioactivities in the palmitate and the stearate are expressed as the percent of the total radioactivity recovered in fatty acids.

TABLE III

Effect of *S. oleracea* Leaf β-ketoacyl-ACP Synthase II on the de novo Synthesis of Fatty Acids in Cell-free Extracts of *S. oleracea* Leaf and of Developing Seeds of *Brassica napus*

| Synthase II Added (fold excess over endogenous) | C16:0 % | C18:0 % |
|---|---|---|
| *S. oleracea* Leaf | | |
| 0 | 58.4 ± 2.7 | 41.6 ± 2.7 |
| 1X | 36.1 ± 0.0 | 57.9 ± 6.1 |
| 2X | 34.3 ± 1.8 | 64.0 ± 0.2 |
| 10X | 10.2 ± 1.0 | 73.0 ± 1.5 |
| Brassica seed | | |
| 0 | 48.0 ± 5.0 | 48.9 ± 1.9 |
| 0.2X | 37.5 ± 1.1 | 59.0 ± 2.6 |
| 0.4X | 37.3 ± 3.4 | 59.8 ± 0.5 |
| 2X | 29.9 ± 1.3 | 68.2 ± 0.7 |

B. Synthase II and Desaturase Experiment

1. Purification of *S. oleracea* Leaf Synthase II

β-ketoacyl-ACP synthase II is partially purified from *S. oleracea* leaves as described above. The synthase II activity from the cellulose phosphate column is concentrated in a Centriprep 30 (Amicon Corporation, Danvers, Mass.). During storage at −70° C., the enzyme loses activity. When this experiment was conducted, the preparation had a specific activity of 10.4 mU/mg protein, and the concentration was 42 mU/ml. Protein was measured by the micro-method of Bradford (supra.) with BioRad Protein Assay Dye Reagent. One unit of activity is defined as the amount of protein required for the incorporation of 1 μmole [2-$^{14}$C]malonate into the reduced product per minute at 37° C.

2. Purification of *C. tinctorius* Seed Δ-9 Desaturase 2.1. Substrate

In each of the following steps, the presence of the enzyme is detected radiometrically by measuring enzyme-catalyzed release of tritium from [9,10(n)-$^3$H]stearoyl-ACP, which is prepared and purified from synthesized [9,10(n)-$^3$H]stearic acid (synthesis described below) by the enzymatic synthesis procedure of Rock, Garwin, and Cronan (*Methods in Enzymol.* (1981) 72:397–403).

[9,10(n)-$^3$H]stearic acid is synthesized by reduction of [9,10(n)-$^3$H]oleic acid with hydrazine hydrate essentially as described by Johnson and Gurr (*Lipids* (1971) 6:78–84). [9,10(n)-$^3$H]oleic acid (2 mCi), supplemented with 5.58 mg unlabeled oleic acid to give a final specific radioactivity of 100 mCi/mmol, is dissolved in 2 ml of acetonitrile, acidified with 40 μl of glacial acetic acid, and heated to 55° C. Reduction is initiated with 100 μl of 60% (w/w) hydrazine hydrate; oxygen is bubbled through the mixture continuously. After each hour acetonitrile is added to bring the volume back to 2 ml and an additional 100 μl of hydrazine hydrate is added. At the end of 5 hr. the reaction is stopped by addition of 3 ml of 2M HCl. The reaction products are extracted with three 3-ml aliquots of petroleum ether and the combined ether extracts are washed with water, dried over sodium sulfate and evaporated to dryness. The dried reaction products are redissolved in 1.0 ml acetonitrile and stored at −20° C. The distribution of fatty acid products in a 15 μl aliquot is determined by preparation of phenacyl esters, which are then analyzed by thin layer chromatography on C-18 reverse phase plates developed with methanol:water::95:5 (v/v). Usually reduction to [9,10(n)-$^3$H]stearic acid is greater than 90%, a small amount of unreacted oleic acid may remain. The analysis is used to establish fraction of the total radioactivity that is present as stearate, and thereby to determine the exact substrate concentration in the enzyme assay.

2.2 Assay. The assay is performed by mixing 150 μl water, 5 ml dithiothreitol (100 mM, freshly prepared in water), 10 μl bovine serum albumin (10 mg/ml in water), 15 μl NADPH (25 mM, freshly prepared in 0.1 M Tricine-HCl, pH 8.2), 25 μl S. oleracea ferredoxin (2 mg/ml Sigma Type III in water), 3 μl NADPH:ferredoxin oxidoreductase (2.5 units/ml from Sigma), and 1 μl bovine liver catalase (800,000 units/ml from Sigma); after 10 min at room temperature, this mixture is added to a 13×100 mm screw-cap test tube containing 250 μl sodium 1,4-piperazinediethanesulfonate (0.1 M, pH 6.0). Finally, 10 μl of the sample to be assayed is added and the reaction is started by adding 30 μl of the substrate, [9,10 (n)-$^3$H]stearoyl-ACP (100 μCi/μmol, 10 μM in 0.1 M sodium 1,4-piperazinediethanesulfonate, pH 5.8). After sealing with a cap, the reaction is allowed to proceed for 10 min. with shaking at 23° C. The reaction is terminated by addition of 1.2 ml of 5.8% tricholoracetic acid and the resulting precipitated acyl-ACPs are removed by centrifugation. The tritium released into the aqueous supernatant fluid by the desaturase reaction is measured by liquid scintillation spectrometry. One unit of activity is defined as the amount of enzyme required to convert one lunit of stearoyl-ACP to oleoyl-ACP, or to release 4 μmol of $^3$H per minute.

2.3 Source tissue. Developing *Carthamus tinctorius* (safflower) seeds from greenhouse grown plants are harvested between 16 and 18 days after flowering, frozen in liquid nitrogen and stored at −70° C. until extracted.

2.4 Acetone Powder Extract. Approximately 50 g of frozen *C. tinctorius* seeds are ground in liquid nitrogen and sieved to remove large seed coat pieces to provide a fine embryo powder. The powder is washed with acetone on a Buchner funnel until all yellow color is absent from the filtrate. The powder is then air dried and further processed as described below, or may be stored frozen for at least a year at −70° C. without loss of enzyme activity. The dried acetone powder is weighed and triturated with ten times its weight of 20 mM potassium phosphate, pH 6.8; the mixture is then centrifuged at 12,000×g for 20 minutes and decanted through a layer of Miracloth (Calbiochem, La Jolla, Calif.).

2.5 Ion Exchange Chromatography. The acetone powder extract is then applied to a DEAE-cellulose column (Whatman DE-52) (1.5×12 cm) equilibrated with 20 mM potassium phosphate, pH 6.8. The pass-through and a wash with one column-volume (20 ml) of buffer are pooled.

2.6 Affinity Chromatography. An affinity matrix for purification of the desaturase is prepared by reacting highly purified *E. coli* ACP, with CNBr-activated Sepharose 4B (Sigma). ACP (120 mg) is reduced by treatment with 1 mM dithiothreitol for 30 min on ice, and then desalted on Sephadex G-10 (Pharmacia) equilibrated with 0.1 M sodium bicarbonate, pH 6.0. The treated ACP (20 ml, 6 mg/ml) is then mixed with 20 ml of CNBr-activated Sepharose 4B swollen in 0.1 M sodium bicarbonate, pH 7.0, and the mixture is allowed to stand at 4° C. for one day. The gel suspension is then centrifuged, washed once with 0.1 M sodium bicarbonate, pH 7.0, and then treated with 40 ml 0.1 M glycine, pH 8.0, for 4 hours at room temperature to block unreacted sites. The gel is then washed for five cycles with alternating 50 ml volumes of 0.5 M NaCl in 0.1 M sodium acetate, pH 4.0, and 0.5 M NaCl in 0.1 M sodium bicarbonate, pH 6.5, to remove non-covalently bound ligand. The gel is loaded into a column (1.5×11.2 cm) and equilibrated in 20 mM potassium phosphate, pH 6.8.

The combined fractions from the DE-52 column are applied to the column, which is subsequently washed with one column volume (20 ml) of the equilibration buffer, and then with 2.5 column volumes (50 ml) of 300 mM potassium phosphate, pH 6.8. Fractions are assayed for protein using the BCA Protein Assay Reagent (Pierce, Rockford, Ill.) to make sure that all extraneous protein has been eluted. Active Δ-9 desaturase is eluted from the column with 600 mM potassium phosphate, pH 6.8. Active fractions are pooled and concentrated using an Amicon 8400 stirred pressure cell. The protein preparation had a specific activity of 0.131 mU/mg protein, and the concentration was 3.15 mU/ml. The desaturase activity is extremely unstable making it necessary to proceed with the experiment immediately following the final step in the desaturase purification.

3. Preparation of cell-free extracts

Cell-free extracts are prepared from *B. napus* seeds as described in Example 1A. Soluble protein is measured by the micro-method of Bradford (supra.) with BioRad Protein Assay Dye Reagent. The *B. napus* extract is assayed for endogenous β-ketoacyl-ACP synthase II activity as described in Example 2, and for endogenous stearoyl desaturase activity as described above. In the Brassica developing seed extract, the synthase II activity was 1280 μU/mg protein; the desaturase activity was 131 μU/mg protein.

4. Fatty Acid Synthetase Reaction

The FAS reaction includes in a 250 μl volume 100 mM HEPES-NaOH buffer, pH 8.0, 2 mM dithiothreitol, 400 μM each NADH and NADPH, 10.4 μM ACP, 12 μM acetyl coenzyme A, 5 μM [2-14C]malonyl coenzyme A (NEN, specific activity 55 Ci/mol), 150 μg Brassica developing seed protein from cell-free extracts, and *S. oleracea* leaf synthase II and/or *C. tinctorius* seed desaturase.

The partially purified β-ketoacyl-ACP synthase II from *S. oleracea* leaf is added to the Brassica seed FAS reaction mix at 2.8- and 12.6-fold excess. The partially purified stearoyl desaturase is added at 2.1- and 9.3-fold excess. The reactions with no exogenous synthase or desaturase contain instead the equivalent volume of the synthase or desaturase buffer. The reactions are incubated for ten minutes at 33° C. and stopped by the addition of 1 ml of hexane-isopropanol (3:2, v:v) and 667 μl sodium sulfate from a 6.67% (w/v) solution. The phases are mixed by vortex for 30 seconds and then separated by centrifugation at 4500×g for one minute. The hexane-isopropanol layer is removed by aspiration, and the sample is re-extracted. The hexane-isopropanol extracts are combined and an aliquot is counted in Aquasol (NEN) in a Beckman LS7800 liquid scintillation counter.

5. Detection

The hexane-isopropanol is evaporated from the extract under a stream of nitrogen gas and the lipids are saponified in 200 μl methanol with 100 μM potassium hydroxide for thirty minutes at 80° C. The saponified lipids are cooled to room temperature and titrated to pH 8.5 with 1 N hydrochloric acid in methanol, to a phenolphthalein endpoint. The methanol is evaporated under a stream of nitrogen gas. Phenacyl esters of the fatty acids in each sample are prepared by incubation with 100 μl p-Bromophenacyl-8 (Pierce, Rockford Ill.) and 100 μl acetonitrile at 80° C. for 30 minutes. The sample is cooled to room temperature, and the solution clarified by centrifugation at 4500×g for five minutes. The supernatant fluid is injected to an Ultrasphere ODS reverse-phase HPLC column (5 micron particle size, 4.6 mm×25 cm) (Beckman, Fullerton, Calif.) equilibrated in 82% acetonitrile in water. The fatty acid phenacyl esters are eluted at two ml per minute in 82% acetonitrile in water for 100 minutes, followed by 25 minutes in 100% acetonitrile. Elution of the exters in monitored by UV absorbance and by radioactivity.

As shown in the tables below, with increasing amounts of S. oleracea leaf synthase II added to the Brassica FAS system, the amount of radioactivity in palmitic acid decreases with a corresponding increase in the radioactivity in stearic acid. With increasing amounts of C. tinctorius seed desaturase, the amount of radioactivity decreases in saturated fatty acids measured (palmitic acid and stearic acid) with a corresponding increase in the amount of radioactivity incorporated into oleic acid. When the largest volume of desaturase is added to the Brassica FAS, the total incorporation of $^{14}$C-malonyl-Coenzyme A into fatty acid decreases. This effect is probably due to components of the desaturase buffer interfering with the in vitro FAS system and therefore limiting the amount of exogenous desaturase that can be added.

TABLE IV

Effects of S. oleracea Leaf β-ketoacyl-ACP Synthase II and C. tinctorius Seed Stearoyl Desaturase on the Incorporation of $^{14}$C Malonyl CoEnzyme A into Lipids by a Cell-free Extract of Developing Seeds of Brassica napus

| Synthase II Added (fold excess over endogenous) | Desaturase Added (fold excess over endogenous) | Incorporation cpm |
|---|---|---|
| 0 | 0 | 20,726 |
| 0 | 2.1 | 20,971 |
| 0 | 9.3 | 10,253 |
| 2.8 | 0 | 20,787 |
| 2.8 | 2.1 | 21,329 |
| 2.8 | 9.3 | 9,629 |
| 12.6 | 0 | 19,650 |
| 12.6 | 2.1 | 19,409 |
| 12.6 | 9.3 | 10,736 |

In the table below, the radioactivities in the individual fatty acids are expressed as the percent of the total radioactivity recovered in fatty acids. The values are averages of duplicate syntheses within one experiment. Repicates were not available for the last two experimental conditions listed in the table.

TABLE V

Effects of S. oleracea Leaf β-ketoacyl-ACP Synthase II and C. tinctorius Seed Δ-9 Desaturase on the Distribution of Fatty Acids Synthesized de novo in a Cell-free Extract of Developing Seeds of Brassica napus

| Synt. II Added (fold excess over endogendus) | Desat. Added | C16:0 % | C18:0 % | C18:1 % |
|---|---|---|---|---|
| 0 | 0 | 12.2 ± 0.4 | 47.3 ± 1.2 | 36.0 ± 0.8 |
| 0 | 2.1 | 11.2 ± 0.6 | 40.3 ± 1.0 | 45.4 ± 0.4 |
| 0 | 9.3 | 17.4 ± 1.3 | 25.6 ± 3.5 | 55.6 ± 3.6 |
| 2.8 | 0 | 6.4 ± 0.3 | 65.6 ± 2.0 | 18.7 ± 1.3 |
| 2.8 | 2.1 | 5.9 ± 0.1 | 64.7 ± 0.1 | 24.8 ± 0.3 |
| 2.8 | 9.3 | 11.5 ± 0.3 | 50.2 ± 1.1 | 30.7 ± 2.0 |
| 12.6 | 0 | 7.1 ± 0.2 | 75.7 ± 0.1 | 6.6 ± 0.7 |
| 12.6 | 2.1 | 6.2 | 77.5 | 10.9 |
| 12.6 | 9.3 | 9.6 | 64.8 | 12.4 |

Example 2
Assay for Synthase Activity

In this example, the assay used to detect synthase activity is described. The presence of the synthase activity is detected radiometrically by modification of the method of Garwin et al.(J. Biol. Chem. (1980) 255:11949–11956), by measuring synthase-catalyzed condensation of [2-$^{14}$C] malonyl-ACP with either decanoyl-ACP (C10-ACP) or hexadecanoyl-ACP (C16-ACP), which produces β-ketododecanoyl-ACP (C12-ACP) or β-ketooctadecanoyl-ACP (C18-ACP), respectively. Products are reduced to their 1,3,-diol forms for extraction into toluene prior to determining incorporation by scintillation counting.

A. Assay

The synthase assay contains 0.2 M potassium phosphate (pH 6.8), 1.25 mM EDTA, 3.1 mM β-mercaptoethanol, 10μ Units malonyl CoA-ACP transacylase (MTA) (purification from E. coli described below), 50 μM ACP (purification from E. coli described below), 100 μM [2-$^{14}$C]malonyl-CoA (20 Ci/mol), 60 μM C16-ACP or C10-ACP, 5% glycerol and enzyme in a total reaction volume of 20 μl.

For maximal activity the MTA and ACP are reduced prior to the enzyme assay by incubation of 1 μl of 1 mM ACP and 0.08 ml of MTA (at 129 μU/ml) in 0.4 μl of 50 mM EDTA, 0.6 μl of 20 mM β-mercaptoethanol, 2 μl of 1 M potassium phosphate, and 1.12 μl of H$_2$O for 15 minutes at 37° C. This solution is then added to a 7.3 μl solution containing 2 μl of 1 M potassium phosphate, 1.3 μl of 1 mM malonyl-CoA and 4 μl of [2-$^{14}$C]malonyl-CoA (47.8 Ci/mol), and the mixed solution is incubated for 2–5 minutes at room temperature to allow MTA to reach equilibrium. Acyl-ACP, either C16-ACP or C10-ACP, in a total volume of 2.5 μl is added to the above solution and the samples are placed at 37° C. The reaction is started by addition of 5 μl of enzyme which is in potassium phosphate buffer (pH 7.5), 20% glycerol (V/V), 1 mM EDTA, and 10 mM β-mercaptoethanol.

The reaction is stopped after 15 minutes by addition of 400 μl of reducing agent containing 0.1 M potassium phosphate, 0.4 M potassium chloride, 30% tetrahydrofuran, and 5 mg/ml NaBH$_4$, with the NaBH$_4$ being added just prior to use. Tubes are vortexed to mix thoroughly after addition of reducing agent and then are incubated for at least 30 minutes (and for up to 3 hours) at 37° C. Toluene, 0.4 ml, is added and samples are again vortexed to mix. Samples are centrifuged for 10 seconds in a microcentrifuge to separate phases. 300 μl of the toluene layer (upper phase) is added to 5 ml Aquasol (NEN Research Products (Dupont) Boston, Mass.) and incorporation of [2-$^{14}$C]malonyl CoA is determined by scintillation counting.

B. Preparation of Assay Components

1. Purification of Acyl Carrier Protein from E. coli 1.1 Assay for ACP. The assay for ACP includes in a volume of 40 μl, 100 mM Tris-HCl, pH8.0, 1% Triton X-100 (w/v)(Boehringer Mannheim Biochemicals, Indianopolis, Ind.), 2 mM dithiothreitol, 5 mM adenosine triphosphate, 20 mM MgCl$_2$, 300 mM LiCl, 33.5 μM [1-$^{14}$C]palmitic acid (NEN Research Products (Dupont), Boston, Mass., specific activity 56 Ci/mol), 32 mU of acyl-ACP synthetase (purified as described below), and 5 μl of ACP source to be assayed. Each assay tube is centrifuged briefly to collect all the liquid into the bottom of the tube, then for three hours at 37° C. From each assay tube 30μl of the 40μl volume is dropped onto a 1 cm$^2$ piece of filter paper, numbered in pencil and suspended on a straight pin. The filters are allowed to air dry for at least 45 minutes, then are washed two times in chloroform:methanol:acetic acid (3:6:1, v:v:v) at the ratio of 15 ml/filter, in a beaker with stirring. The filters are placed into scintillation vials and counted in 5 ml Aquasol in a Beckman LS3801 liquid scintillation counter (Beckman, Fullerton, Calif.). A one-to-one stoichiometry is assumed between ACP and the 1-$^{14}$C-palmitate with the product, $^{14}$C-palmitoyl-ACP, bound to the filter, and the free fatty acid washed into the organic solvent.

1.2 Extraction and Purification of ACP. The acyl carrier protein (ACP) is purified from E. coli strain K-12 by a modification of the method of Rock and Cronan, (*Methods in Enzymol.* (1981) 71:341–351). The *E. coli* is obtainable from Grain Processing Corporation (Muscatine, Iowa) as frozen late-logarithmic phase cells. One kilogram of frozen packed cells of *E. coli* K12 is thawed overnight at 4° C. At room temperature, the cells are combined with 1 L deionized water, 500 mg lysozyme (from chicken egg white, Sigma), and 200 ml lysis buffer containing 1M Tris-HCl, 1M glycine, 250 mM sodium EDTA, pH 8.0. This is stirred at room temperature by a Wheaton overhead stirrer. After two hours, 5 g of Triton X-100 is added and stirring is continued for another hour. The suspension is further homogenized by blending in a 6 L Waring Model CB6 Commercial Blender for 60 seconds. Stirring of the homogenate is resumed and 2 L of isopropanol are added from a separatory funnel in a thin stream over twenty minutes to ensure immediate mixing.

Immediately after the addition of the isopropanol, the homogenate is clarified by centrifugation at 10,000×g for 30 minutes at room temperature. The pH of the supernatant fluid is adjusted to 6.5 with glacial acetic acid and this is combined with 440 ml of a 50% slurry of Whatman DE52 (Whatman, Clifton, N.J.) in 10 mM (bis[2-hydroxyethyl] imino-tris[hydroxymethyl]-methane hydrochloride (Bis-Tris-Hcl) (Sigma, St. Louis, Mo.), pH 6.5. It is important to sediment the precipitate and combine the supernatant with the DE52 as quickly as possible to prevent clogging of the filters and the column in subsequent steps. The DE52 slurry is allowed to stir overnight or for at least one hour at room temperature, and is then filtered on a sintered glass funnel. The DE52 in the filter funnel is washed five times with 200 ml 10 mM Bis-Tris-Hcl, 2 mM DTT, 0.1% (w/v) TX-100, and four times with 200 ml 10 mM Bis-Tris-Hcl, 2 mM DTT, 250 mM LiCl. It is resuspended in 200 ml of the last wash buffer and poured into a 4.8 cm×40 cm column. The flow-through is collected in bulk. The ACP is eluted at 2 ml/min with 10 mM Bis-Tris-Hcl, 2 mM DTT, 600 mM LiCl; 6 ml fractions are collected.

After it was determined by the radiometric assay that the ACP fractions also contain a yellow contaminant, the ACP fractions were selected for pooling by their yellow color. The fractions are pooled into a centrifuge bottle and with stirring on ice, the ACP is precipitated by the dropwise addition of 50% ice cold trichloroacetic acid (TCA) to a final concentration of 5% TCA. The protein is quickly sedimented by centrifugation at 10,000×g for 30 minutes at 4° C.

The pellet is suspended in 10 ml deionized water, and solubilized by the addition of 500 μl aliquots of 1 M Tris base, with homogenization in a hand-held ground glass homogenizer after each addition. At pH 7.0, the solution is clear. The volume is brought to 50 ml with deionized water, and contaminating protein is precipitated by the addition of 26.15 g (80% saturation) solid ammonium sulfate with stirring on ice over 45 minutes. Stirring is continued for one hour on ice, and the protein is sedimented by centrifugation at 23,700×g for 45 minutes. The ACP is concentrated by precipitation with trichloroacetic acid and resolubilized with Tris base as described above, keeping the final volume to about 5 ml or less. The solution is clarified by centrifugation at 20,000×g for 20 minutes at 4° C. A typical yield of ACP is 80–100 mg from 1 kg packed cells of *E. coil* K12.

2. Purification of Malonyl Coenzyme A:Acyl Carrier Protein Transacylase (MTA) from *E. coli*

2.1 MTA Assay. The MTA activity is measured at room temperature by modification of the the assay of Alberts et al. (*Methods in Enzymol.* (1969) 14:53–56). The reaction mix of 100 μl includes 100 mM potassium phosphate buffer, pH 6.5, 100 μM ACP, 100 μM malonyl coenzymeA (Sigma), 10 nCi [2-$^{14}$C]malonyl coenzyme A (specific activity 43.1 Ci/mol, NEN), 2 mM β-mercaptoethanol and enzyme in 10 μl. The ACP is incubated with an equal volume of 20 mM β-mercaptoethanol for 15 minutes before being added to the rest of the reaction mix excluding the enzyme. The reaction is started by the addition of enzyme, incubated for 4 minutes at 23° C., and stopped by the addition of 400 μl ice cold 5% perchloric (v/v) acid. The reaction is held on ice for at least 20 minutes. The precipitate is collected on a Millipore HA, 0.45 micron filter on a Millipore filtration manifold (Millipore, Bedford, Mass.). The precipitate from each assay tube is washed on the filter three times with 5 ml ice cold 5% (v/v) perchloric acid. The filters are dropped into 5 ml Aquasol (NEN) without neutralization or drying, and are counted in a Beckman LS3801 Liquid Scintillation Counter (Beckman, Fullerton, calif.). One unit of MTA activity is defined as the conversion of 1 μmole of acid-soluble malonate to acid-precipitable malonate per minute. Protein determinations are by the micromethod of Bradford (*Analy. Biochem.* (1976) 72:248–254), using Bio-Rad Protein Assay Dye Reagent (Bio-Rad, Richmond, Calif.).

2.2 Extraction and Purification of MTA. The MTA is purified from *E. coli* by a modification of the method of Alberts et al. (*Methods in Enzymol.* (1969) 14:53–56). All steps of the purification are carried out at 4° C. Fractions are routinely stored overnight at 4° C. between steps of the protocol. Frozen packed cells (20 g) of *E. coli* K12 available from Grain Processing Corporation (Muscatine, Iowa) are thawed overnight, then suspended in 20 ml Buffer A which contains 10 mM Tris-HCl, 1 mM sodium EDTA and 10 mM β-mercaptoethanol at pH 7.5. The cells are ruptured by two passes through a French Pressure Cell (American Instrument Company, Silver Spring, Md.) at 16,000 psi. The broken cells are diluted with 40 ml of Buffer A and the particulates are sedimented by centrifugation at 16,000×g for 30 minutes. The supernatant is combined with streptomycin sulfate (Sigma) from a 20% solution in Buffer A (w/v) for a final concentration of 60 mg streptomycin sulfate per milliliter. The precipitate is sedimented immediately by centrifugation at 17,500×g for 15 minutes. The supernatant fluid is diluted with three volumes of Buffer B, which contains 10 mM potassium phosphate, 1 mM sodium EDTA and 10 mM β-mercaptoethanol at pH 7.0, and applied at 360 ml/h to a 4.8 cm×11 cm column of DEAE Fast-Flow (Pharmacia, Piscataway, N.J.) equilibrated in Buffer B. The column is washed with two bed volumes of Buffer B containing 75 mM LiCl. The MTA activity is eluted with a two-bed volume gradient of Buffer B containing 75–250 mM LiCl.

The fractions containing peak MTA activity, at about 240 mM LiCl, are pooled and non-MTA protein is precipitated by the addition of solid ammonium sulfate (29.5 g/100 ml.) The suspension is stirred for 30 minutes, then clarified by centrifugation at 16,000×g for 30 minutes. The MTA activity is precipitated by the addition of solid ammonium sulfate to the supernatant fluid (19.7 g/100 ml.) which is stirred and sedimented by centrifugation as above. The pellet is suspended with 10 ml Buffer C, containing 20 mM potassium phosphate, 1 mM sodium EDTA and 10 mM β-mercaptoethanol at pH 7.0 and applied to a 2.5 cm×40 cm column of Sephadex G-100 (Pharmacia Inc., Piscataway, N.J.) equilibrated in Buffer C. The protein is eluted at 60 ml/h. The fractions containing peak MTA activity are pooled and applied at 60 ml/h to a 2.5 cm×4.7 cm column of DEAE Fast-Flow in Buffer D, which is Buffer C containing 150 mM LiCl. The column is washed with three bed volumes of Buffer D, then a 4-bed volume gradient of Buffer C containing 150–300 mM LiCl is applied. The MTA activity elutes in the 150 mM LiCl wash rather than in the LiCl gradient as was described by Alberts et al. (supra) The fractions containing peak MTA activity are pooled and the protein is precipitated by the addition of ammonium sulfate (61.1 g/100 ml.) The suspension is stirred for one hour and the precipitated MTA activity is collected by centrifugation at 16,000×g for one hour. The pellet is dissolved in 0.5 ml Buffer C and dialysed overnight against one liter of Buffer C. The dialysate is stored as aliquots in polypropylene tubes at −70° C.

About 3.7 units of MTA activity are produced from 20 g of packed cells by this method. When stored at −70° C., as a concentrate of 2.5 U/ml, the MTA retains 100% of its activity for at least 18 months. For the β-ketoacyl-ACP synthase assay, it is diluted into "20 buffer" (described below in Example 3) containing 10 mM β-mercaptoethanol.

3. Purification of Acyl-Acyl Carrier Protein Synthetase

Acyl-ACP synthetase is purified according to the method of Rock and Cronan, 1979, *J. Biol Chem*, Vol 254 No. 15:7116–7122, with the following changes. The heat treatment is eliminated. The fraction from the Blue-Sepharose column is applied at 240 ml/hour to a 2.4 cm×40 cm column of BioGel P-6DG (Bio-Rad, Richmond, Calif.) equilibrated in 5 mM Tris-HCl, pH 8.0 with 2% (w/v) Triton X-100. Throughout the purification, protein levels are determined with the Micro BCA Protein Reagent from Pierce (Rockford, Ill.).

Although quite variable, the yield of acetyl-ACP synthetase is about 55 units from 125 g *E. coli* K12 packed cells. One unit of activity is described as the amount of protein required to produce 1 nmol of C16:0-ACP from palmitate and ACP per minute. During storage at 4° C., a precipitate is formed that must be suspended before use.

4. Synthesis and Purification of Acyl-Acyl Carrier Protein

The C10:0-ACP and C16:0-ACP substrates are synthesized enzymatically and are purified by the procedure of Rock et al. (*Methods in Enzymol.* (1981) 72:397–403). The acyl-ACP substrates for the β-ketoacyl synthase I and II assays require no radiolabel, but sufficient $^{14}C$ or $^{3}H$ may be included to monitor the purification after the enzymatic synthesis. The yield of acyl-ACP is also monitored by the filter assay method described by Rock et al. (supra). The synthetic reaction includes, in a 10 ml volume, 4.8 μmol palmitic or decanoic free fatty acid, 800,000 cpm [9,10-$^{3}$H] palmitic acid (NEN Research Products (Dupont), Boston, Mass., specific activity 28.5 Ci/mmol) or [1-$^{14}$C]decanoic acid (ICN Biomedicals, Inc, Costa Mesa, Calif., specific activity 3.6 Ci/mol), 100 mM Tris-HCl pH 8.0, 5 mM adenosine 5'-triphosphate, 2 mM dithiothreitol, 2% Triton X-100 (Boehringer Mannheim Biochemicals, Indianopolis, Ind.), 400 mM LiCl, 10 mM $MgCl_2$, 15 mg ACP and 3 units acyl-ACP synthetase. The mix is incubated at 37° C. for three hours and may be stored at room temperature for about 15 hours or at −20° C. until purification.

The purification of the acyl-ACP from the synthetic mix is carried out at room temperature according to the procedure of Rock et al. (supra) with the following changes. The wash with 2-propanol is omitted as it was found that the free fatty acid does not bind to the DE-52 column. The volume of the wash of the DE-52 with equilibration buffer, however, is increased to ensure removal of the Triton X-100. Some lots of Octyl-Sepharose (Pharmacia Inc., Piscataway, N.J.) do not allow adsorption of the acyl-ACP. A test column is therefore run with each new lot of the resin. In most cases, 50% 2-propanol is required for complete recovery of the acyl-ACP. The second DE-52 column is omitted; instead, the acyl-ACP in 50% 2-propanol is brought to dryness by lyophilization or in a SpeedVac Concentrator (Savant Instruments Inc, Hicksville, N.Y.), and is reconstituted with deionized water. The substrates are stored at −70° C.

Typical yields are 1.7 μmol of palmitoyl-ACP or 0.5 μmol of decanoyl-ACP.

Example 3
Purification of Synthase Proteins

In this example, purification of β-ketoacyl-ACP synthase from developing seeds of *Ricinus communis* is described. All steps of protein purification are done at 4° C. or on ice. Until the ricin, a toxic seed protein, has been removed, all steps are done in a glove box or with appropriate precautions to prevent exposure to the toxin.

A. Extraction

1. Source tissue

*Ricinus communis* is grown in the greenhouse under the following conditions.

temperature range is 22–32° C.

lighting is set for a 16-hour day length (supplemental lighting is with high pressure sodium lamps)

fertilizer is 60 ppm nitrogen daily via watering The developing seeds are harvested at 21 to 28 days after the flowers open. The endosperm is removed and frozen in liquid nitrogen, and is stored at −70° C. for up to 18 months until used for purification of synthase activity.

2. Purification Buffers

The buffers used in the purification of β-ketoacyl-ACP synthases are at pH 7.5, and contain 20% (v/v) glycerol, 1 mM sodium EDTA, 10 mM β-mercaptoethanol, and potassium phosphate at the millimolar concentration that is designated in the buffer name. For example, "20 buffer" contains 20 mM potassium phosphate. The exception is "zero buffer", which is lacking only in the potassium phosphate, and has a pH of approximately 5.

3. Extraction Procedure

A 200 g batch of frozen tissue is homogenized in an Osterizer blender for 15 seconds at top speed in 400 ml of "40 buffer" which also contains the following protease inhibitors: 1 mM amino caproic acid, 1 μM leupeptin, 1 μM pepstatin, and 100 μM phenylmethylsulfonyl fluoride. Blending is limited to 15 seconds to prevent release of too much of the seed lipid, which if present would interfere with the subsequent ammonium sulfate fractionation. The crude homogenate is clarified by centrifugation at 16,000×g for one hour. The supernatant fluid, Fraction A, contains the solubilized β-ketoacyl-ACP synthase activity.

B. Ammonium Sulfate Fractionation

Fraction A, is decanted through cheesecloth and Miracloth (CalBiochem, La Jolla, Calif.) and stirred with ammonium sulfate (40.4 g/100 ml) for one hour. The precipitated protein is sedimented by centrifugation at 16,000×g for one hour. The supernatant fluid, Fraction B, containing the β-ketoacyl-ACP synthase activity, is stirred with ammonium sulfate (13.4 g/100 ml) for one hour and the protein sedimented by centrifugation at 16,000×g for one hour. This ammonium sulfate pellet, Fraction D, is suspended in a minimal volume of "20 buffer" and stored at −70° C.

C. Reactive Green 19 Agarose Chromatography

Fraction D is diluted with "20 buffer" to a final volume of 1650 ml. Fraction D is then combined with 200 ml (packed bed volume) Reactive Green 19-agarose (Sigma, St. Louis, Mo.) which has been pre-equilibrated in "20 buffer", and this solution is stirred by an overhead stirrer for two hours. The Green 19-agarose is filtered on a sintered glass funnel and washed with 200 ml of "50 buffer". The washed Green 19-agarose is suspended in an additional 175 ml of "50 buffer" and is poured into a 4.8 cm×30 cm column. The agarose is packed at 200 ml/hr, until the last of the "50 buffer" reaches the top of the Green 19-agarose bed. The synthase activity is then eluted with "250 buffer". The synthase activity elutes in the first 100 ml of "250 buffer". The fractions are stored at −20° C. until the next step of purification.

D. ACP-Affinity Chromatography

An affinity matrix for purification of the synthase activities is prepared by reacting highly purified E. coli ACP, with CNBr-activated Sepharose 4B by modification of the procedure of McKeon and Stumpf (J. Biol. Chem. (1982) 257:12141–12147) as described below.

1. Matrix Preparation

E. coli ACP, 141 mg in a volume of 40 ml, is dialyzed against 3 volumes of 1 liter of 100 mM $NaHCO_3$, pH 6.0, for 24 hours in Spectrapor #7 dialysis tubing (molecular weight cutoff=2000). One millimolar dithiothreitol is included in the second buffer change only, for a total of 3 hours. One hundred milliliters of 1 mM HCl is added to 6.0 g of CNBr-activated Sepharose in a 250 ml polypropylene centrifuge bottle. This is mixed at high speed for 15 minutes at room temperature on a "Rugged Rotator" (Kraft Apparatus, Inc., Mineola, N.Y.) ferris-wheel type mixer. The resulting slurry is poured into a Kontes (Vineland, N.J.) 2.5 cm×20 cm column and is washed with 1.1 liter of 1 mM HCl at 250 ml/hr, at room temperature for the first two hours and then at 4° C. The CNBr-activated Sepharose is then washed in a 60 ml sintered glass funnel five times with 20 ml 100 mM $NaHCO_3$, pH 6.0, followed by 5 times with 20 ml 100 mM $NaHCO_3$, pH 7.0. The CNBr-activated Sepharose is then resuspended in 40 ml of 100 mM $NaHCO_3$, pH 7.0, and transferred to a clean 250 ml polypropylene centrifuge bottle. The dialyzed ACP is added to the CNBr-activated Sepharose slurry and the suspension is mixed for 24 hours at 4° C. on the "Rugged Rotator" mixer to couple the ACP to the CNBr-activated Sepharose. The ACP-Sepharose is sedimented by centrifugation for 6 minutes at 100×g (800 rpm in a Beckman GP tabletop swinging bucket centrifuge) at 4° C. The supernatant fluid is removed and saved for assay. Fifty milliliters of 1 M ethanolamine at pH 8.0 is added to the ACP-Sepharose and mixed on the "Rugged Rotator" at 4° C. for 16 hours to block unused binding sites.

2. Column Packing

The ACP-Sepharose gel is poured into a 2.5 cm×20 cm column and is washed with 100 ml of 100 mM $NaHCO_3$, pH 7.0 containing 500 mM NaCl, followed by another wash with 100 ml of 100 mM sodium acetate, pH 4.0 containing 500 mM NaCl. This washing with alternate buffers is repeated three times. The gel is then washed with 200 ml of the bicarbonate buffer, and finally with 200 ml of "20 buffer" plus 0.02% sodium azide. The gel is left in this buffer until further use. The unbound fractions were assayed for protein by the method of Bradford (Analy. Biochem. (1976) 72:248–254) and it was calculated that 134 mg of the ACP had bound to the 25 ml CNBr-activated Sepharose. Before application of protein sample, the ACP-Sepharose is packed into a 2.5 cm×10 cm column and washed with 250 ml "20 buffer". Final volume of the packed bed is 25 ml.

3. Sample Preparation

The fractions from the Green 19-agarose chromatography with synthase activity are combined in an Amicon 8400 stirred pressure cell apparatus with a PM30 membrane (Amicon, Danvers, Mass.). The emptied fraction tubes are rinsed with an equal volume of "zero buffer" and the rinse is added to the pooled fractions. Pressure is applied via nitrogen gas until the volume of the concentrate is 10% of the original solution volume. The pressure is then released and the stirring is continued for an additional 5 mins. The concentrate is diluted with "zero buffer" until the conductivity reaches that of "10 buffer", as measured with a Beckman conductivity meter.

4. Chromatography of Fractions from Green-19 Agarose

The diluted sample containing synthase activity is loaded onto the ACP-Sepharose column at a flow rate of 100 ml per hour, and the column is washed with one bed volume of "20 buffer". The flow-through and the "20 buffer" wash are collected in bulk, and 6 ml fractions are collected during elution. The protein is eluted at 25 ml per hour with five bed volumes of "100 buffer" followed by a ten bed volume gradient of "250 buffer". Following the gradient, the column is washed with additional "500 buffer" until a total of 72 fractions have been collected. The column is regenerated by washing with 10 bed volumes of "500 buffer", followed by 10 bed volumes of "20 buffer". When not in use, the column is stored in "20 buffer" containing 0.02% sodium azide as a preservative.

5. Assay of Fractions for Synthase Activity

The fractions were assayed for both C16-ACP and C10-ACP condensing activities. The major peak of C16-ACP condensing activity eluted in fractions 32–44. A portion of the C10-ACP activity eluted with the major C16-ACP condensing activity peak, but the bulk of the C10-ACP condensing activity eluted after the C16-ACP peak, sometimes as a broad shoulder to the initial peak, and sometimes as a separate peak.

E. SDS-PAGE Analysis and Separation of Peptides

The fractions of the ACP-Sepharose column are analyzed by polyacrylamide gel electrophoresis in sodium dodecyl sulfate (SDS-PAGE) by a variation of the method of Laemmli (Nature (1970) 227:680–685). The resolving gel contains only 0.2% bis-acrylamide instead of the standard 0.267%. A Bio-Rad (Richmond, Calif.) Protean II mini-gel unit is used at 200V. The current is allowed to flow until the tracking dye reaches the end of the gel, and then for an additional 10 minutes. This allows better separation of the two major peptide bands. Fractions in the first peak of synthase activity, which contains the majority of the C16-ACP condensing activity, contain both a 46 kD and a 50 kD band with approximately equal silver-staining intensities. The bulk of the C10-ACP condensing activity, which elutes after the C16-ACP condensing activity, is associated with a more faintly staining 50 kD band. The synthase fractions are pooled, concentrated and desalted and the proteins are separated in bulk by SDS-PAGE electrophoresis as described. From 200 g, fresh weight, of embryonic seed tissue, approximately 50 µg of each of the 46 kD and 50 kD proteins is recovered.

F. Purification Table

Protein recovery and synthese activity at each step of purification are presented in the tables below.

TABLE VI

Purification of *R. communis* β-ketoacyl-ACP synthase I

|  | Total Protein (Bradford) mg | Protein Recovery % | Total Activity mol/min | Activity Recovery % | Specific Activity mol/min/mg | Purifition-fold |
|---|---|---|---|---|---|---|
| crude extract | 1059.4 | 100.00 | 13.3 | 100.00 | .012 | 1.0 |
| 0–60% ammonium sulfate (supernatant) | 386.6 | 36.49 | 33.1 | 249.12 | .086 | 6.8 |
| sat'd ammonium sulfate (pellet) | 149.5 | 14.11 | 9.7 | 72.75 | .065 | 5.2 |
| Green-19 Agarose | 18.3 | 1.73 | .97 | 7.31 | .053 | 4.2 |
| ACP-Sepharose "Peak Two" (affinity chromatography) | 0.01* | 0.00 | .16 | 1.22 | 16.2 | 1290.3 |

*rough estimate from Laemmli SDS-PAGE gel

TABLE VII

Purification of *R. communis* β-ketoacyl-ACP Synthase II

|  | Total Protein (Bradford) mg | Protein Recovery % | Total Activity mol/min | Activity Recovery % | Specific Activity mol/min/mg | Purifition-fold |
|---|---|---|---|---|---|---|
| crude extract | 1059.4 | 100.00 | 17.5 | 100.00 | .016 | 1.0 |
| 0–60% ammonium sulfate (supernatant) | 386.6 | 36.49 | 12.8 | 73.35 | .033 | 2.0 |
| sat'd ammonium sulfate (pellet) | 149.5 | 14.11 | 10.0 | 57.26 | .067 | 4.1 |
| Green-19 Agarose | 18.3 | 1.73 | .93 | 5.29 | .051 | 3.1 |
| ACP-Sepharose (affinity chromatography) | 0.09* | 0.01 | .15 | 0.87 | 1.70 | 102.9 |

*rough estimate from Laemmli SDS-PAGE gel

G. Electroblotting from SDS-PAGE

1. Gel Electrophoresis

Material from the ACP-Sepharose column is applied to a 1.5 mm thick SDS reduced cross-linker mini-polyacrylamide gels prepared as described above in Example 3E. The resolving gel is poured the night before the gels are run; the stacking gel is poured the same day. Each ACP-Sepharose column pool contains 40–60 μg of protein. The protein is divided between 2 gels of 10 wells each, with each lane containing 2–3 μg of protein. The gels are run as described above in Example 3E. After electrophoresis, the gels are assembled into a Bio-Rad Mini Trans-Blot module (Bio-Rad, Richmond, Calif.) and the protein is electroblotted to either nitrocellulose or polyvinylidenefluoride (PVDF) membranes.

2. Blotting to Nitrocellulose

When protein is electroblotted to nitrocellulose, the blotting time is 1 hour and the buffer used is 25 mM Tris, 192 mM glycine in 20% methanol. Following electroblotting to nitrocellulose, membranes are stained in 0.1% (w/v) Ponceau S in 1% (v/v) acetic acid for 2 minutes and destained in 2–3 changes of 0.1% (v/v) acetic acid, 2 minutes for each change. Following this, nitrocellulose membranes are stored wet in heat-sealed plastic bags at −20° C. Originally, nitrocellulose membranes were destained in 1% acetic acid and then rinsed with HPLC grade water prior to storage. The stained bands fade rapidly in neutral pH however, so the destain solution was changed to 0.1% acetic acid and membranes were also stored wetted in this solution. If time permits, blots are not frozen but used immediately for digestion to create peptides for determination of amino acid sequence as described below.

3. Blotting to PVDF

When protein is electroblotted to PVDF, the blotting time is 30 minutes and the buffer used is 125 mM Tris/50 mM glycine in 10% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. Following this, PVDF membranes are allowed to air dry for 30 minutes and are then stored dry in heat-sealed plastic bags at −20° C. Protein blotted to PVDF is used directly to determine N-terminal sequence of the intact protein.

Example 4

Determination of Amino Acid Sequence

In this example, a method for the determination of the amino acid sequence of a plant β-ketoacyl-ACP synthase is described.

A. Digestion

Proteins blotted to nitrocellulose are subjected to digestion with proteases in order to obtain peptides for sequencing. The method used is that of Aebersold, et al. (*PNAS* (1987) 84:6970). Bands of both the 46 kD and 50 kD proteins, and also an equal amount of blank nitrocellulose to be used as a control, are cut out of the nitrocellulose membrane, chopped into pieces 1×2 mm in size, and washed several times with HPLC grade water in order to remove the Ponceau S. The Ponceau S is not always removable if the blot has been frozen, but the presence of the stain apparently has no effect on the digest procedure. Following this wash, 1.0–1.2 ml of 0.5% polyvinylpyrrolidone (PVP-40, Aldrich, Milwaukee, Wis.) in 0.5% acetic acid is added to the membrane pieces and this mixture is incubated for 30 minutes at 37° C. The PVP-40 is needed to block sites on the nitrocellulose which would bind the protease and/or peptides released by the protease digestion. Following treatment with PVP-40, the membrane pieces are rinsed with several 1.0 ml volumes of HPLC grade water to remove excess PVP-40. The pieces are then suspended in either trypsin digest buffer, 100 mM sodium carbonate pH 8.2, or endoproteinase gluC buffer, 25 mM ammonium carbonate/1 mM EDTA, pH 7.8. Acetonitrile is added to the digest mixture to a concentration of 5% (v/v). Protease, trypson or endoproteinase glu C is diluted in digest buffer and added to the digest mixture in a ratio of 1:10 (w/w) protease to protein. Final volume of the digest mixture is 100 µl. Digests are incubated overnight. Trypsin digests are incubated at 37° C. and endoproteinase gluC digests are incubated at room temperature.

B. Separation of Peptides

Following overnight incubation, digest reactions are stopped by the addition of 10 µl 10% (v/v) trifluoroacetic acid (TFA). The digest mixture is removed from the nitrocellulose pieces, the nitrocellulose pieces are washed with 1–5 100 µl volumes of 0.05% (v/v) TFA, and these volumes are concentrated to a volume of less than 100 µl in a Speed-Vac (Savant; Farmingdale, N.Y.). These concentrates are then injected over a Vydac reverse phase Protein & Peptide C18 column (2.1 mm×100 mm) installed in an Applied Biosystems (Foster City, Calif.) Model 130 High Performance Liquid Chromatograph (HPLC). Mobile phases used to elute peptides were: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 µl/minute is used. Peptides are detected at 214 nm, collected by hand, and then stored at −20° C.

In early digestion experiments, the PVP-40 was incompletely removed and eluted as a broad peak at 50% buffer B. Very few peptides were recovered from these runs. The PVP-40 peak was collected and then treated with an equal volume of chloroform to extract the PVP-40. The aqueous material was then reapplied to an Applied Biosystems HPLC, as above, except in this case buffer A was 0.1% TFA, buffer B was 0.1% TFA in acetonitrile, and the column used was an Applied Biosystems (Foster City, Calif.) reverse phase Spheri-5 RP18 column (1 mm×50 mm). The gradient and flow rate were as above and the peaks were detected, collected and stored in the same manner.

In later digestion experiments, PVP-40 was thoroughly removed and no chloroform extraction was necessary. In order to remove the PVP-40 completely, nitrocellulose pieces are washed with many volumes of water (8×4 ml), checking the absorbance of the washes at 214 nm on a spectrophotometer. Also, PVP-40 is more easily removed if bands are not cut into small pieces until after PVP-40 treatment and washing. These two modifications eliminate interference problems with the PVP-40.

3. Reduction & Alkylation of Cysteine Residues

Digested protein can be reduced with β-mercaptoethanol and alkylated with $^3$H-labelled iodoacetic acid as a method to improve identification of cysteine residues when the peptides are sequenced. The β-mercaptoethanol is added to freshly digested protein at a molar ratio of 20:1 over the assumed concentration of sulfhydryl groups in the sample and peptides are incubated at room temperature for 30 minutes. $^3$H-labelled iodoacetic acid is then added at a concentration of 1.1 times the concentration of β-mercaptoethanol and the peptides are incubated in dark-ness (covered with foil) at room temperature for 60 minutes. To stop the alklylation, more β-mercaptoethanol is added at a concentration of one-tenth of that used to reduce the peptides. Ten µl of 10% TFA is then added as usual to stop any further action of the protease. This can not be added prior to the reduction/alkylation as those reactions work best under the basic pH conditions present in the digest mixture. The reduced/alkylated protein is then concentrated in a Speed-Vac prior to separation of the peptides by HPLC, as described above.

4. N-terminal Sequencing of Proteins & Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored on to the on-board computer of the sequencer and also on to a Digital Microvax using ACCESS*CHROM software from PE NELSON, Inc (Cupertino, Calif.). Sequence data is read from a chart recorder, which receives input from the PTA Analyzer, and is confirmed using quantitative data obtained from the sequencer on-board computer system. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTA-amino acid product material from each sequencer cycle is counted in a liquid scintillation counter. For protein samples which have been electroblotted to PVDF, the band of interest is cut out and then placed above a Polybrene coated glass fiber filter, pre-cycled as above and the reaction cartridge is assembled according to manufacturer's specifications.

In order to obtain protein sequences from small amounts of sample (5–30 pmoles), the 477A conversion cycle and the 120A analyzer as described by Tempst and Riviere (*Anals. Biochem.* (1989) 183:290).

Fragments generated from the trypsin and gluC digestion steps are presented in FIGS. 2 and 3. Other proteases may be used to digest the synthase proteins, including but not limited to lysC and aspN. While the individual digest buffer conditions may be different, the protocols for digestion, peptide separation, purification, and sequencing are substantially the same as those outlined for the digestions with trypsin and gluc. Alternatively, synthases may be digested chemically using cyanogen bromide (*Gross Methods Enzymol* (1967) 11:238–255 or Gross and Witkop *J. Am. Chem. Soc.* (1961) 83:1510), hydroxylamine (Bornstein and Balian *Methods Enzymol.* (1977) 47:132–745), iodosobenzoic acid (*Inglis Methods Enzymol.* (1983) 91:324–332), or mild acid (Fontana et al., *Methods Enzymol.* (1983) 91:311–317), as described in the respective references.

Example 5

Methods to Distinguish Synthase Proteins

In this example, a method to selectively label synthase proteins with cerulenin and a method to express synthase activity in a prokaryote are described.

A. Cerulenin Labeling

1. Distinguishing Synthase I and II using Cerulenin

Cerulenin has been shown to bind to the active sites of synthase I and synthase II. In *S. oleracea,* at a concentration of five µM, cerulenin reacts readily with the active site of synthase I but not synthase II. Cerulenin will react readily, however with both synthase I and synthase II at concentrations above 50 µM (Shimakata and Stumpf, *Proc.Nat.Acad. Sci.* (1982) 79:5805–5812). Cerulenin shows similar reaction with synthase I and synthase II of *R. communis* as shown in FIG. 1. To differentially radiolabel synthase I and synthase II for subsequent gel analysis and protein sequencing to determine the active sites, $^3$H-cerulenin is reacted with concentrated post-ACP-sepharose (Example 3) protein containing synthase activity at two different $^3$H-cerulenin concentrations. The samples are then run on Laemmli SDS-PAGE and the molecular weights of the $^3$H-labeled proteins are determined by scintillation counting. Candidate bands, containing both protein and $^3$H-label, are digested with endoproteinase gluC and the peptides are separated and sequenced via Edman chemistry.

2. Preparation of Radiolabeled Cerulenin

[3H]-Cerulenin (specific activity=585 Ci/mol) was prepared from unlabeled cerulenin (Sigma) by Amersham (Arlington Heights, Ill.) tritium labeling service. The material is purified by HPLC.

3. Labeling Synthase I $^3$H-cerulenin is prepared for use by measuring out the required amount of $^3$H-cerulenin solution (in methanol) necessary to make 1.0 mls of 5 µM solution (5 nmoles) into a screw-cap microfuge tube. The methanol is then evaporated under a stream of nitrogen, chasing with a diethyl ether to ensure complete evaporation of the methanol. The tube is capped and the dry $^3$H-cerulenin is stored on ice until use (see below).

Material from ACP-Sepharose "Peak One" which contains both the 46 kD and 50 kD proteins is pooled and concentrated in an Amicon stirred pressure cell with a PM10 43 mm membrane. The concentrate is diluted in the cell with "zero" buffer (described in Example 3 A.2) and reconcentrated to desalt the material. The material is desalted to a phosphate concentration of approximately 20 mM. Initial volume of the pooled fractions is 60–66 mls and the volume of the final concentrate is 1.0 ml or less, which represents a 40-fold or greater concentration.

The concentrated, desalted material is removed from the Amicon stirred cell to the microfuge tube containing the 3H-cerulenin and additional "20" buffer (described in Example 3 A.2) is added to a final volume of 1 ml. The mixture is incubated at 37° C. for 20 minutes to allow complete reaction with the synthase I.

4. Labeling Synthase II

To label synthase II with $^3$H-cerulenin in a mixture of synthase I and synthase II, synthase I must first be blocked with unlabeled cerulenin. Five nmoles of unlabeled cerulenin is prepared as described above for the $^3$H-cerulenin. $^3$H-cerulenin is prepared as above except a larger concentration is used to ensure binding to synthase II.

The concentrated enzyme is prepared as above and reacted first with 5 µM unlabeled cerulenin for 20 mins at 37° C. to block the synthase I from subsequent reaction with the $^3$H-cerulenin. Following this reaction, the sample is placed in the second tube containing the higher concentration of $^3$H-cerulenin and reacted at 37° C. for 60 mins. The rest of the procedure is as described above.

5. Gel Analysis of Candidate Protein Fractions

Laemmli-SDS-PAGE methods are as described in Example 3E, again using the reduced cross-linker formula for the gels. Gel thickness is 0.75 mm. Bands from SDS-PAGE are excised and analyzed by scintillation counting to determine the molecular weight of labeled bands, and amino acid sequence of labeled fragments is determined.

6. Sequence Determination

The protein is digested with endoproteinase gluC using the method described in Example 4, with the following alteration. The digestion is carried out in solution, therefore the 5% acetonitrile added to previous digests for ease in recovery of peptides off of nitrocellulose is omitted. Reverse-phase HPLC and sequencing of peptides are as described in Example 4.

B. *E. coli* Expression

1. Expression Vectors

Plasmids for expression of β-ketoacyl-ACP synthase activity in *E. coli* can be constructed using one or more *E. coli* expression vectors. These expression vectors include pUC120, an *E. coli* expression vector based on pUC118 (Vieria and Messing, *Methods in Enzymology* (1987) 153:3–11) with the lac region inserted in the opposite orientation and an NcoI site at the ATG of the lac peptide (Vieira, J. PhD. Thesis, University of Minnesota, 1988). Other expression vectors which may be used include, but are not limited to, the pET system vectors, in particular pET8C (Studier et al., *Methods in Enzymology* (1990) ed. D. V. Goedel, Vol. 185) which use a T7 RNA polymerase promoter, and pKK223 vector (Pharamacia), which utilizes a trp-lac (tac) bacterial promoter. An example of *E. coli* expression of synthase activity associated with a 50 kD protein using the pUC120 expression system is described below.

2. Constructs for Expression of Synthases

A fragment containing regions of a cDNA which encodes the 50 kD protein associated with synthase activity, can be subcloned into pUC120 using commercially available linkers, restriction endonucleases, and ligase. The subcloned regions will include the coding region of the mature protein, and also possibly 5' and 3'-noncoding sequences, a transit peptide sequence, and a poly(A) tail. The synthase sequences are inserted such that they are aligned in the 5' to 3' orientation with the lac transcription and translation signals. The resulting plasmid can be transformed to an appropriate strain of *E. coli* for analysis.

Constructs containing the cDNA clone for the 46 kD protein or containing the cDNAs for both the 46 kD and the 50 kD proteins can be made using the procedures and vectors described above.

3. Expression of Synthase Activity in *E.coli*

Single colonies of *E. coli* containing pUC120 or the synthase constructs in pUC120 are cultured in ECLB broth containing 300 mg/L penicillin. The cells are induced by the addition of 1 mM IPTG. Cells are grown overnight (18 hrs) at 37° C. The overnight cultures of *E. coli* (induced and uninduced) containing pUC120 or the synthase constructs in pUC120 are centrifuged to pellet the cells. The pelleted cells are resuspended in buffer and broken in a french press at 16,000 psi. Broken cell mixtures are centrifuged and a portion of each supernatant is applied to a G-25 Sephadex gel filtration centrifugal column (Boehringer Mannheim Biochemicals), equilibrated buffer. Columns are centrifuged and effluent is collected and used as enzyme source in the synthase assay. Synthase activity is assayed as described in Example 2. Cerulinin is also reacted with the synthase activity to distinguish synthase I and synthase II activities as described previously in Example 5A.

4. Detection of Synthase Protein in *E. coli*

Extracts of overnight cultures of *E. coli* containing pUC120 or synthase constructs in pUC120 grown in ECLB containing 300 mg/L penicillin induced with 1 mM IPTG are prepared as follows. Overnight cultures grown shaking at 37° C. are pelleted by centrifugation in 1.5 ml Eppendorf tubes. Pellets are resuspended in SDS sample buffer (0.05M Tris-HCl, pH6.8, 1% SDS, 5% β-mercaptoethanol, 10% glycerol and 0.005% bromophenol blue) and boiled for 10 min. Samples are electrophoresed on a 10% polyacrylamide gel (Laemmli, *Nature* (1970) 227:680). Gels are stained in 0.05% Coomassie Brilliant Blue, 25% isopropanol and 10% acetic acid and destained in 10% acetic acid and 10% isopropanol. Bands corresponding to synthase proteins may be detected by comparison of *E. coli* proteins produced in cells containing synthase constructs inserted in pUC120 to those containing the pUC120 vector with no insertion.

Example 6
Isolation of Synthase Genes

In this example, the preparation of a cDNA libraries, using the methods as described in Alexander, et al. (*Methods in Enzymology* (1987) 154:41–64), and the screening of the cDNA libraries for synthase cDNA clones are described.

A. *R. communis* cDNA Library Construction

A cDNA library may be constructed from poly(A)+ RNA isolated from *R. communis* immature endosperm from seeds collected at approximately 14–21 days post-anthesis. Total RNA is isolated from 10 g of *R. communis* immature endosperm tissue by a method described by Halling, et al. (*Nucl. Acids Res.* (1985) 13:8019–8033). Total RNA is furthur purified by removing polysaccharides on a 0.25 g Sigma Cell 50 cellulose column. The RNA is loaded onto the column in 1 ml of loading buffer (20 mM Tris-HCl pH 7.5, 0.5 M NaCl, 1 mM EDTA, 0.1% SDS), eluted with loading buffer, and collected in 500 µl fractions. Ethanol is added to the samples to precipitate the RNA. The samples are centrifuged, and the pellets resuspended in sterile distilled water, pooled, and again precipitated in ethanol. The sample is centrifuged, and the resulting RNA is subjected to oligo (dT)-cellulose chromatography two times to enrich for poly (A)+ RNA as described by Maniatis et al. (*Molecular Cloning: A Laboratory Manual,* Cold Spring Harbor Laboratory, New York (1982)).

The plasmid cloning vector pCGN1703, derived from the commercial cloning vector Bluescribe M13– (Stratagene Cloning Systems; San Diego, Calif.), is made as follows. The polylinker of Bluescribe M13– is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with synthetic complementary oligonucleotides having the sequences 5' CGGATCCACTGCAGTCTAGAGGGCCCGGGA 3' and 5' AATTTCCCGGGCCCTCTAGACTGCAGTG-GATCCGAGCT 3'. These sequences are inserted to eliminate the EcoRI site, move the BamHI site onto the opposite side of the SstI (also, sometimes referred to as "SacI" herein) site found in Bluescribe, and to include new restriction sites PstI, XbaI, ApaI, SmaI. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang sticky-ends using terminal deoxynucleotidyl transferase. The tailed plasmid is separated from undigested or un-tailed plasmid by oligo(dA)-cellulose chromatography. The resultant vector serves as the primer for synthesis of cDNA first strands from mRNA covalently attached to either end of the vector plasmid by their poly(A) tract. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI sticky-end at one end and a G-tail at the other. This complex is cyclized using the annealed synthetic cyclizing linker, 5'-GATCCGCGGCCGCGAATTCGAGCTCCCCCCCC CC-3' and 3'-GCGCCGGCGCTTAAGCTCGA-5' which has a BamHI sticky-end and a C-tail end. Following ligation and repair the circular complexes are transformed into *E. coli* strain DH5α (BRL; Gaithersburg, Md.) to generate the cDNA library. The *R. communis* immature endosperm cDNA bank contains approximately $2 \times 10^6$ clones with an average cDNA insert size of approximately 1000 base pairs.

B. Isolation of a *R. communis* cDNA Clone to the 50 kD Synthase Protein

1. Probe Production 1.1 Polymerase Chain Reactions (PCR). Amino acid sequences from two peptides from the 50 kD synthase amino acid sequence (Example 3) with low codon degeneracy, KR4 and KR16 are chosen for production of a probe for the plant 50 kD synthase cDNA. Four sets of mixed oligonucleotides are designed and synthesized for use as forward and reverse primers in the polymerase chain reaction (Saiki et al., *Science* (1985) 230:1350–1354; Oste, *Biotechniques* (1988) 6:162–167) for the KR4 sequence, and two sets of mixed oligonucleotides are designed and synthesized for use as forward and reverse primers in the polymerase chain reaction for the KR16 sequence. All oligonucleotides are synthesized on an Applied Biosystems 380A DNA synthesizer.

The KR4 oligonucleotide groups have a redundancy of 128 and contain 20 bases of coding sequence along with flanking restriction site sequences for HindIII (forward primers) or EcoRI (reverse primers). The KR16 oligonucleotide groups have a redundancy of 384 and contain 23 bases of coding sequence along with flanking restriction site sequences for HindIII (forward primers) or EcoRI (reverse primers). The KR4 forward and KR16 reverse primers are illustrated in FIG. 4.

The KR4 oligonucleotide groups are combined so that only two polymerase chain reactions are required to account for both possible orientations of the KR4 and KR16 peptides in the synthase protein. Using the cDNA library DNA as template and the possible two combinations of the forward and reverse oligonucleotides as primers, polymerase chain reactions are performed in a Perkin-Elmer/Cetus DNA Thermal Cycler (Norwalk, Conn.) (thermocycle file 1 min. 94° C., 2 min. 42° C., 2 min rise from 42°–72° C., 3 min. 72° C. for 15 cycles, followed by the step cycle file without step rises, 1 min. 94° C., 2 min. 42° C., 3 min. 72° C. with increasing 15 sec extensions of the 72° C. step for 10 cycles, and a final 10 min. 72° C. extension).

1.2 PCR Product Analysis 1.2.1 Subcloning. The 283 bp product of the KR4 forward primer and the KR16 reverse primer reaction is gel-purified, digested with HindIII and EcoRI, and ethanol precipitated. The resulting fragment is subcloned into pCGN2015, a chloramphenicol resistant version of Bluescript KS+ (Stratagene, La Jolla, Calif.).

1.2.2 Construction of pCGN2015. pCGN2015 is prepared by digesting pCGN565 with HhaI, and the fragment containing the chloramphenicol resistance gene is excised, blunted by use of mung bean nuclease, and inserted into the EcoRV site of Bluescript KS– (Stratagene, La Jolla, Calif.) to create pCGN2008. pCGN565 is a cloning vector based on pUC12-cm (K. Buckley Ph.D. Thesis, Regulation and expression of the phi X174 lysis gene, University of California, San Diego, 1985), but contains pUC18 linkers (Yanisch-Perron, et al., *Gene* (1985) 53:103–119). The chloramphenical resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015.

1.2.3 Clone Analysis. Minipreparation DNA (Maniatis et al., supra) of two clones, AG-18 and AG-32, was sequenced by Sanger dideoxy sequencing (Sanger et al., *Proc. Nat. Acad. Sci. USA* (1977) 74:5463–5467) using the M13 universal and reverse primers. The clones were shown to have the same DNA sequence. Translation of the DNA sequence results in an amino acid sequence that contains five of the 50 kD synthase peptides (78 amino acid residues) within its 91 amino acid residues. The translated amino acid sequence was shown to have homology to the β-ketoacyl-ACP synthase I gene of *E. coli* which is encoded by fabB (Kauppinen et al., *Carlsberg Res. Commun.* (1988) 53:357–370), and a polyketide synthase gene from *Streptomyces glaucescins* which has been shown to have homology to other β-ketoacyl synthases (Bibb et al., *EMBO J.* (1989) 8:2727–2736).

1.3 Probe Purification. The 283 bp insert in AG-32 was amplified by PCR using the minipreparation DNA as template and the KR4 and KR16 oligonucleotides described above as primers. The resulting fragment was gel-purified for use as a probe in screening cDNA library screening.

2. Library Screen

The *R. communis* immature endosperm cDNA bank is moved into the cloning vector lambda gt22 (Stratagene Cloning Systems, La Jolla, Calif.) by digestion of total cDNA with NotI and ligation to lambda gt22 DNA digested with NotI. The titer of the resulting library was approximately $1.5 \times 10^7$ pfu/ml. The library is then plated on *E. coli* strain Y1090 (Young, R. A. and Davis, R. W., *Proc. Natl. Acad. Sci. USA* (1983) 80:1194 at a density of approximately 15,000 plaques/150 mm NZY ("NZYM" as defined in Maniatis et al. supra) agar plate to provide over 60,000 plaques for screening. Duplicate lifts are taken of the plaques using NEN Colony Plaque Screen filters by laying precut filters over the plates for approximately 2 minutes and then peeling them off. The phage DNA is immobilized by floating the filters on denaturing solution (1.5 M NaCl, 0.5 M NaOH) for 1 min., transferring the filters to neutralizing solution (1.5 M NaCl, 0.5 M Tris-HCI pH 8.0) for 2 min. and then to 2×SSC (1×SSC=0.15 M NaCl; 0.015 M Na citrate) for 3 min., followed by air drying. The filters are prehybridized at 42° C. in hybridization buffer consisting of 50% formamide, 10×Denhardts solution, 5×SSC. 1% SDS, 5 mM EDTA, and 0.1 mg/ml denatured salmon sperm DNA. Filters are hybridized overnight at 42° C. in the same buffer solution with added $^{32}$P-labeled (Boehringer Mannheim Random Primed DNA Labeling Kit) AG-32 insert DNA described above. Filters are washed sequentially at 55° C. in 1×SSC, 0.1% SDS for 25 minutes, in 0.5×SSC, 0.1% SDS for 25 minutes, and finally in 0.1×SSC, 0.1% SDS for 25 minutes. Filters are exposed to X-ray film at −70° C. with a Dupont Cronex intensifying screen for 48 hours.

3. Clone Analysis

Clones are detected by hybridization with the AG-32 $^{32}$P-labeled DNA and plaque purified. Phage DNA is prepared from the purified clones as described by Grossberger (*NAR* (1987) 15:6737) with the following modification. The proteinase K treatment is replaced by the addition of 10% SDS and a 10 minute incubation at room temperature. Recovered phage DNA is digested with NotI, religated at low concentration, and transformed into *E. coli* mm294 (Hanahan, *J.Mol.Biol.* (1983) 166:557–580) cells to recover plasmids containing cDNA inserts in pCGN1703. Preliminary nucleotide sequence of the cDNA insert of the longest clone, pCGN2764(1-3), indicates that the clone does not contain the entire coding sequence for the gene.

4. Screening for Longer Clones

Longer cDNA clones can be obtained by screening the *R. communis* cDNA library with an oligonucleotide from the furthest 5' sequence of this clone.

A 23 base oligonucleotide, #2272, was synthesized which consists of the sequence 5' ACCAGCAACAATGCAATAC-CTCA 3', which is complementary to nucleotides 24–46 of CDNA clone pCGN2764. Greater than 100,000 clones from the *R. communis* embryo cDNA library in lambda gt22 are plated in *E. coli* strain Y1090 as described above at a density of 20,000 plaques/150 mm NZY plate. Phage are lifted onto NEN Colony/Plaque Screen filters as described above. The probe for hybridization is prepared by 5' end-labeling oligonucleotide #2272 using BRL 5× buffer and T4 kinase. Filters are prehybridized and hybridized with the probe at 37° C., and washed to remove background hybridization according to the method of Berent et al. (*BioTechniques* (1985) 3:208–220). Filters are exposed to X-ray film at −70° C. with a Dupont Cronex intensifying screen overnight.

12 clones are detected by hybridization to the oligonucleotide probe and are plaque-purified and recovered as pCGN1703 plasmids as described above. Minipreparation DNA (Maniatis et al., supra) from each of the clones is analyzed by restriction digestion and agarose gel electrophoresis. The complete DNA sequence of the longest clone, pCGN2765(2-8), is presented in FIG. 5. DNA sequence is determined by the dideoxy-chain termination method of Sanger et. al, (*Proc. Natl. Acad. Sci. USA* (1977) 74:5463–5467) using the 7-Deaza-dGTP Reagent Kit with Sequenase Version 2 Enzyme (United States Biochemical Corp., Cleveland, Ohio). The sequence data are analyzed using the IntelliGenetics Suite of molecular programs Gel and SEQ.

C. Isolation of a *R. communis* CDNA Clone for the 46 kD Synthase Protein

1. Probe Production 1.1 Polymerase Chain Reactions. A probe to be used in screening for a cDNA clone to the 46 kD protein can be prepared by PCR from oligonucleotides to the 46 kD peptide sequences following the procedures described above in the isolation of a cDNA to the 50 kD protein. Sequences derived from the N-terminal peptide amino acid sequence of the 46 kD protein, KHPLMXQRRVVVTGMGV, (sequences used for oligo design indicated in bold letters) are used as the forward primers in four polymerase chain reactions. The reverse primers for these reactions are DNA sequences derived from 46 kD peptides KR2, EEVNYINAXATSTPAGDL, and KR3, VFNDAIEALR. The forward primer has a redundancy of 128 and contains 20 bases of coding sequence along with a flanking HindIII restriction site (AAGCTT). The reverse primers have a redundancy of 128 (KR2) and 64 (KR3) and contain 20 bases of coding sequence along with flanking sequences specifying EcoRI restriction sites (GAATTC). These restriction sites are useful in cloning the product resulting from PCR. Reactions are performed in a Perkin-Elmer/Cetus DNA Thermal Cycler (Norwalk, Conn.) (step cycle file 1 min. 94° C., 2 min. 50° C., 3 min. 72° C. for 15 cycles, followed by the step cycle file, 1 min. 94° C., 2 min. 42° C., 3 min. 72° C. with increasing 15 sec extensions of the 72° C. step for 10 cycles, and a final 10 min. 72° C. extension). PCR using NTERM-B, 5'TTTAAGCTTAAPCAQCCNCTNATGAAPCA3', as forward primer, and KR2-A, 5'TTTGAATTCTTPATPTAPTT-NACQTCQTC3' or KR3-A, 5'TTTGAATTCGCQTCTATNGCPTCPTTPAA3', as reverse primers, where N=A,G,C or T, Q=C or T, and P=A or G, resulted in production of prominent ~900 bp and ~330 bp bands, respectively.

1.2 Analysis of PCR products. A nitrocellulose filter containing PCR product DNA was prepared by the Southern blot technique (Maniatis et al., supra) The filter was probed with a synthetic oligonucleotide, Nterm11, 5'ACNCCCAT-NCCNGT3' prepared from the 46 kD N-terminal sequence KHPLMKQRRVVVTGMGV. Nterm-11 is derived from a different portion of the N-terminal sequence than the oligonucleotide used as forward primer in the reactions. Prehybridization, hybridization, and washing of the filter is according to Berent et al. (supra.), the only significant change being in the temperature used for hybridization and prehybridization, which was 25° C. Both the ~900 bp and ~330 bp bands produced by PCR as described above hybridize to this oligonucleotide. Furthur evidence that the ~330 bp band is a product specific to a cDNA for the 46 kD protein is obtained by repeating the PCR described above with the Nterm-B and KR3-A oligonucleotides, but using the product from the Nterm-B/KR2-A PCR as template. The ~330 bp band is again obtained as the predominant product. The ~330 bp PCR product is digested with HindIII and EcoRI and subcloned into pCGN2015 as described above. Mini-preparation DNA is prepared and DNA sequence of clones containing the ~330 bp fragment is determined as described above.

1.3 Probe Purification. The ~330 bp PCR product is gel-purified for use as probe in screening the cDNA library.

2. Library Screen

The R. communis embryo cDNA library described above can be screened for a cDNA to the 46 kD synthase protein using the procedures described above in the isolation of a cDNA to the 50 kD synthase. The ~330 bp DNA fragment described above is $^{32}$P-labeled using a randon primed labeling kit (Boehringer Mannheim). Greater than 60,000 clones in lambda gt22 are plated at a density of approximately 15,000/150 mm NZY plate and lifted onto NEN Colony/Plaque Screen filters as described above. Clones are detected by hybridization to the ~330 bp PCR fragment by prehybridization, hybridization, and washing as described above for screening for the cDNA to the 50 kD protein using the AG-32 fragment as probe. Clones are plaque-purified, lambda DNA is isolated, and clones are recovered as E. coli clones containing plasmids with inserts in pCGN1703 as described above. DNA sequence of clones is determined as described above.

D. Isolation of Synthase Genes from Other Plant Sources

1. B. campestris cDNA Library Construction

Total RNA is isolated from 5 g of B. campestris cv. R500 embryos obtained from seeds harvested at days 17–19 post-anthesis. RNA is extracted in 25 mls of 4 M guanidine thiocyanate buffer as described by Colbert et al.(PNAS (1983) 80:2248–2252). Polysaccharides are removed from the RNA sample by resuspending the pellet in 6 ml of 1×TE (10 mM Tris/1 mM EDTA pH 8), adding potassium acetate to a concentration of 0.05 M, and adding one half volume of ethanol. The sample is placed on ice for 60 minutes and centrifuged for 10 minutes at 3000×g. RNA is precipitated from the supernatant by adding sodium acetate to a concentration of 0.3 M followed by the addition of two volumes of ethanol. RNA is recovered from the sample by centrifugation at 12,000×g for 10 minutes and yield calculated by UV spectrophotometry. Two mg of the total RNA is further purified by removing polysaccharides as described in Example 6A. The resulting RNA is enriched for poly(A)+ RNA also as described in Example 6A.

A Brassica campestris day 17–19 post anthesis embryo cDNA library is constructed in plasmid vector pCGN1703 using 5 µg of poly(A)+ RNA as described in Example 6A. cDNA libraries from other plant sources can be similarly prepared.

2. Genomic Library Construction

Genomic libraries can be constructed from DNA from various plant sources using commercially available vectors and published DNA isolation, fractionation, and cloning procedures. For example, a B. campestris genomic library can be constructed using DNA isolated according to Scofield and Crouch (J.Biol.Chem. (1987) 262:12202–12208) that is digested with BamHI and fractionated on sucrose gradients (Maniatis et al., supra), and cloned into the lambda phage vector LambdaGem-11 (Promega; Madison, Wis.) using cloning procedures of Maniatis et al. (supra).

3. Screening cDNA and Genomic Libraries cDNA and genomic libraries can be screened for synthase cDNA and genomic clones, respectively, using published hybridization techniques. Screening techniques are described above for screening libraries with radiolabeled oligonucleotides and longer DNA fragments. Probes for the library screening can be prepared by PCR, or from the sequence of the synthase clones provided herein. Oligo-nucleotides prepared from the synthase sequences may be used, as well as longer DNA fragments, up to the entire synthase clone.

Example 7

Synthase Constructs in Plants

In this example, constructs containing R. communis synthase gene(s) suitable for plant transformation are described.

A. Expression Cassettes

Expression cassettes utilizing 5'-upstream sequences and 3'-downstream sequences of genes preferentially expressed during seed development can be constructed from isolated DNA sequences of genes with an appropriate expression pattern. Examples of genes which are expressed during seed development in Brassica are a napin gene, 1-2, and an ACP gene, Bcg4-4, both described in European Patent Publication EP 0 255 378, and a Bce4 gene, as described below. The napin gene encodes a seed storage protein that is preferentially expressed in immature embryos which are actively producing storage proteins. The ACP gene encodes a protein which is an integral factor in the synthesis of fatty acids in the developing embryo and is preferentially expressed during fatty acid synthesis. Bce4 is a gene that produces a protein of unknown function that is preferentially expressed early in embryo development, at about 15–19 days post-anthesis, and is also detectable as early as 11 days post-anthesis. The sequence of Bce4 is shown in FIG. 7. The 5' and 3' regulatory sequences are obtainable from a genomic library of B. campestris, which can be constructed as described in Example 6D.

DNA sequences that control the expression of these genes can be isolated and sufficient portions of the 5' and 3' regulatory regions combined such that a synthase gene inserted between these sequences will be preferentially expressed early in seed development. This expression pattern will allow the synthase gene to affect fatty acid synthesis, which also occurs early in seed development. For example, a 1.45 kb XhoI fragment containing 5' sequence and a 1.5 kb SstI/BglII fragment containing 3' sequence of the Bcg4-4 ACP gene can be combined in an ACP expression cassette using a variety of available DNA manipulation techniques. Similarly, a napin expression cassette can be prepared that contains approximately 1.725 kb of 5' sequence from an EcoRV site to immediately before the ATG start codon and approximately 1.25 kb of 3' sequence from an XhoI site approximately 18 bases past the TAG stop codon to a 3' HindIII site of a 1-2 napin gene. A Bce4 expression cassette can be made by combining approximately 7.4 kb of 5' DNA sequence from an upstream PstI site to immediately before the ATG start codon with approximately 1.9 kb of 3' sequences from immediately after the TAA stop codon to a 3' PstI site.

Variations can be made in these expression cassettes such as increasing or decreasing the amounts of 5' and 3' sequences, combining the 5' sequences of one gene with the 3' sequences of a different gene (for example using the 1.3 kb 5' sequences of napin 1-2 with the 1.5 kb 3' sequences of ACP Bcg4-4 in an expression cassette), or using other available 3' regulatory sequences, as long as these variations result in expresion cassettes that allow for expression of the inserted synthase gene at an appropriate time during seed development.

B. Synthase Constructs in Plants

1. Insertion of Synthase Gene into Expression Cassettes

Synthase cDNA sequences from isolated cDNA clones can be inserted in the expression cassettes in either the sense or anti-sense orientation using a variety of DNA manipulation techniques. If convenient restriction sites are present in the synthase clones, they may be inserted into the expression cassette by digesting with the restriction endonucleases and ligation into the cassette that has been digested at one or more of the available cloning sites. If convenient restriction sites are not available in the clones, the DNA of either the cassette or the synthase gene(s), can be modified in a variety of ways to facillitate cloning of the synthase gene(s) into the cassette. Examples of methods to modify the DNA include by PCR, synthetic linker or adaptor ligation, in vitro site-directed mutagenesis (Adelman et al., supra), filling in or cutting back of overhanging 5' or 3' ends, and the like. These and other methods of manipulating DNA are well known to those of ordinary skill in the art.

2. Binary Vectors for Plant Transformation

The fragment containing the synthase gene in the expression cassette, 5' sequences/synthase/3' sequences, can be cloned into a binary vector such as described by McBride and Summerfelt (*Pl.Mol.Biol.* (1990) 14:269–276) for Agrobacterium transformation. Other binary vectors are known in the art and may also be used for synthase cassettes.

The binary vector containing the expression cassette and the synthase gene is transformed into *Agrobacterium tumefaciens* strain EHA101 (Hood, et al., *J. Bacteriol.* (1986) 168:1291–1301) as per the method of Holsters, et al., (*Mol. Gen. Genet.* (1978) 163:181–187) for plant transformation as described in Example 9.

3. Other Methods of Plant Transformation

The binary vectors described above are useful for Agrobacterium-mediated plant transformation methods. Other methods for plant transformation, such as the DNA-bombardment technique described in Example 9B, and electroporation may be used as well.

4. Constructs Containing More than One Synthase Gene

If more than one synthase gene is required to obtain an optimum effect in plants, the genes may be expressed under regulation of two different promoters that are preferentially expressed in developing seeds, such as the napin, ACP, and Bce4 sequences described above, and introduced into plants in the same binary vector, or introduced simutaneously in different binary vectors. Use of more than one binary vector would require the use of additional selectable markers to allow for selection of both genes. Examples of selectable markers that can be used include the nptII gene for kanamycin resistance, which is used in the binary vectors of McBride and Summerfelt (supra), the nitrilase gene, bxn, that confers resistance to the herbicide bromoxynil, described by Stalker et al. (*Science* (1988) 242:419–423), and a gene that confers resistance to the antibiotic hygromycin, (van den Elzen et al., *Pl.Mol.Biol.* (1985) 5:299–302). Other selectable markers are also known and can be used in binary vectors for plant transformation. Alternatively, the genes can be introduced into the plant sequentially by transforming a plant expressing one of the desired genes with a construct containing a second desired gene. This method would also require the use of a different selectable marker for selection of the second gene.

Another alternative for obtaining expression of more than one synthase gene in a transformed plant is to produce by the methods described above, different plants, each of which is expressing one of the synthase genes. A plant expressing both genes can be obtained by plant breeding techniques.

Example 8

Plants Transformed with Synthase and Desaturase

In this example constructs containing a desaturase gene isolated from *C. tinctorius* are described. The complete cDNA sequence of the *C. tinctorius* desaturase clone, pCGN2754, is presented in FIG. 8.

A. Desaturase Gene in an ACP Expression Cassette

The preparation of an ACP expression cassette containing *C. tinctorius* Δ-9 desaturase in a binary vector suitable for plant transformation is described.

An expression cassette utilizing 5'-upstream sequences and 3'-downstream sequences obtainable from *B. campestris* ACP gene can be constructed as follows.

A 1.45 kb XhoI fragment of Bcg 4-4 containing 5'-upstream sequences is subcloned into the cloning/sequencing vector Bluescript+ (Stratagene Cloning Systems, San Diego, Calif.). The resulting construct, pCGN1941, is digested with XhoI and ligated to a chloramphenicol resistant Bluescript M13+ vector, pCGN2015 digested with XhoI. pCGN2015 described in Example 6. This alters the antibiotic resistance of the plasmid from penicillin resistance to chloramphenicol resistance. The chloramphenicol resistant plasmid is pCGN1953.

3'-sequences of Bcg 4-4 are contained on an SstI/BglII fragment cloned in the SstI/BamHI sites of M13 Bluescript+ vector. This plasmid is named pCGN1940. pCGN1940 is modified by in vitro site-directed mutagenesis (Adelman et al., *DNA* (1983) 2:183–193) using the synthetic oligonucleotide 5'-CTTAAGAAGTAACCCGGGCTGCAGTTTTAGTAT TAAGAG-3' to insert SmaI and PstI restriction sites immediately following the stop codon of the reading frame for the ACP gene 18 nucleotides from the SstI site. The 3'-noncoding sequences from this modified plasmid, pCGN1950, are moved as a PsI-SmaI fragment into pCGN1953 cut with PstI and SmaI. The resulting plasmid pCGN1977 comprises the ACP expression cassette with the unique restriction sites EcoRV, EcoRI and PstI available between the 1.45 kb 5' and 1.5 kb of 3'-noncoding sequences for the cloning of genes to be expressed under regulation of these ACP gene regions.

Desaturase cDNA sequences from pCGN2754 are inserted in the ACP expression cassette, pCGN1977, as follows. pCGN2754 is digested with HindIII (located 160 nucleotides upstream of the start codon) and Asp718 located in the polylinker outside the poly(A) tails. The fragment containing the coding region for desaturase was blunt-ended using DNA polymerase I and ligated to pCGN1977 digested with EcoRV. A clone containing the desaturase sequences in the sense orientation with respect to the ACP promoter is selected and called pCGN1895. The fragment containing the pCGN1895 expression sequences ACP 5'/desaturase/ACP 3' is cloned into a binary vector pCGN1557 (described below) for Agrobacterium transformation by digestion with Asp718 and XbaI and ligation to pCGN1557 digested with Asp718 and XbaI. The resulting binary vector is called pCGN1898.

B. Desaturase in an Anti-Sense Construct

Cassettes for transcription of antisense constructs include, but are not limited to the seed preferential expression cassettes described in Example 7. An antisense construct is described below which allows for constitutive transcription of a *B. campestris* desaturase cDNA clone in the 5' to 3' orientation of transcription such that the mRNA strand produced is complementary to that of the endogenous desaturase gene.

1. Isolation of *B. campestris* Desaturase cDNA cDNA clones for desaturase are isolated from the *B. campestris* cDNA library described in Example 6 D.1. Partial DNA sequence of two clones, pCGN3235 and pCGN3236, are presented in FIGS. 9A and 9B, respectively. Initial DNA sequence analysis of the 3' regions of these clones indicates that pCGN3235 and pCGN3236 are cDNA clones from the same gene. pCGN3236 is a shorter clone than pCGN3235, which appears to contain the entire coding region of the *B. campestris* desaturase gene.

2. Binary Vector Construction

The KpnI, BamHI, and XbaI sites of binary vector pCGN1559 (McBride and Summerfelt, *Pl.Mol.Biol.* (1990) 14: 269–276) are removed by Asp718/XbaI digestion followed by blunting the ends and recircularization to produce pCGP67. The 1.84 kb PstI/HindIII fragment of pCGN986 containing the 35S promoter-tml3' cassette is inserted into PstI/HindIII digested pCGP67 to produce pCGP291.

The 35S promoter-tml3' expression cassette, pCGN986, contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7144–7734) (Gardner et. al., *Nucl.Acids Res.* (1981) 9:2871–2888) into the HincII site of M13mp7 (Messing, et. al., *Nucl.Acids Res.* (1981) 9:309–321) to create C614. An EcoRI digest of C614 produced the EcoRI fragment from C614 containing the 35S promoter which is cloned into the EcoRI site of pUC8 (Vieira and Messing, *Gene* (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct, pCGN528, is made as follows: pCGN525 is made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et. al., *Cell* (1980) 19:729–739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMB9KanXXI is a pUC4K variant (Vieira and Messing, *Gene* (1982) 19:259–268) which has the XhoI site missing, but contains a functional kanamycin gene from Tn903 to allow for efficient selection in Agrobacterium.

pCGN149a is digested with HindIII and BamHI and ligated to pUC8 digested with HindIII and BamHI to produce pCGN169. This removes the Tn903 kanamycin marker. pCGN565 (described in Example 6) and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204, an EcoRI fragment of CaMV (bp 408–6105) containing the region VI 3' cloned into pUC18 (Yanisch-Perron, et al., *Gene* (1985) 33:103–119) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., (1980) supra) as a BamHI-EcoRI fragment (nucleotides 9062 to 12,823, numbering as in Barker et al., *Plant Mol. Biol.* (1982) 2:335–350) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207–9023 of the T-DNA).

3. Insertion of Desaturase Sequence

The 1.6 kb XbaI fragment from a *B. campestris* desaturase cDNA clone, pCGN3235, which contains the desaturase cDNA is inserted in the antisense orientation into the XbaI site of pCGP291 to produce pCGN3234. A desaturase construct is transformed into a desired plant host using any appropriate method, such as described in Example 9.

C. Synthase and Desaturase Constructs in Plants

Plants containing both a synthase construct as described in Example 7 and a desaturase construct, such as those described above, may be prepared using any appropriate transformation method, such as those described in Example 9. The constructs may be combined in a common binary vector, when Agrobacterium is used for plant transformation, or introduced into a plant simultaneously on different binary vectors using different selectable markers. Also, plants containing synthase and desaturase constructs may be prepared by retransformation of a plant that contains one of the desired sequences, with a construct containing the other desired sequence.

Another alternative for obtaining expression of more than one synthase gene in a transformed plant is to produce by the methods described above, different plants, each of which is expressing one of the synthase genes. A plant expressing both genes can be obtained by plant breeding techniques.

Example 9

In this example, an Agrobacterium-mediated plant transformation is described and *Brassica napus* is exemplified. Also, a DNA-bombardment plant transformation is described and peanut transformation is exemplified.

A. Transformation of *B. napus*

Seeds of *Brassica napus* cv. Delta are soaked in 95% ethanol for 2 min, surface sterilized in a 1.0% solution of sodium hypochlorite containing a drop of Tween 20 for 45 min., and rinsed three times in sterile, distilled water. Seeds are then plated in Magenta boxes with ⅒th concentration of Murashige minimal organics medium (Gibco) supplemented with pyridoxine (50 μg/l), nicotinic acid (50 μg/1), glycine (200 μg/l), and 0.6% Phytagar (Gibco) pH 5.8. Seeds are germinated in a culture room at 22° C. in a 16 h photoperiod with cool fluorescent and red light of intensity approximately 65 μEinsteins per square meter per second ($\mu Em^{-2}S^{-1}$).

Hypocotyls are excised from 7 day old seedlings, cut into pieces approximately 4 mm in length, and plated on feeder plates (Horsch et al. 1985). Feeder plates are prepared one day before use by plating 1.0 ml of a tobacco suspension culture onto a petri plate (100×25 mm) containing about 30 ml MS salt base (Carolina Biological) 100 mg/l inositol, 1.3 mg/l thiamine-HCl, 200 mg $KH_2PO_4$ with 3% sucrose, 2,4-D (1.0 mg/l), 0.6% Phytagar, and pH adjusted to 5.8 prior to autoclaving (MSO/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA101 containing a binary plasmid are transferred to 5 ml MG/L broth and grown overnight at 30° C. Per liter, MG/L broth contains 5 g mannitol, 1 g L-glutamic acid or 1.15 g sodium glutamate, 0.25 g $kH_2PO_4$, 0.10 g NaCL, 0.10 g $MGSO_4.7H_2O$, 1 mg biotin, 5 g tryptone, and 2.5 g yeast extract, and the broth is adjusted to pH 7.0. Hypocotyl explants are immersed in 7–12 ml MG/L broth with bacteria diluted to $1\times10^8$ bacteria/ml and after 10–20 min. are placed onto feeder plates. After 48 h of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim) at concentrations of 25 mg/l.

After 3–7 days in culture at 65 $\mu Em^{-2}S^{-1}$ to 75 $\mu Em^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% Phytagar) and placed in a culture room with conditions as described for seed germination. After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for NPT II activity.

B. Peanut Transformation

DNA sequences of interest may be introduced as expression cassettes, comprising at least a promoter region, a gene of interest, and a termination region, into a plant genome via particle bombardment as described in European Patent Application 332 855 and in co-pending application U.S. Ser. No. 07/225,332, filed Jul. 27, 1988.

Briefly, tungsten or gold particles of a size ranging from 0.51 μM–3 μM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bomardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 μM to 300 μM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg.l 6-benzyladenine (BA) for the cotyledon segments) and incubated in the dark for 1 week at 25±2° C. and are subsequently transferred to continuous cool white fluorescent light (6.8 W/m²). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods known to those skilled in the art.

The above results demonstrate the ability to obtain protein preparations with synthases activities, especially synthase I or synthase II, isolate DNA sequences related to such protein preparations and manipulate them. In this manner, the production of transcription constructs and expression cassettes can be produced which allow for production, especially differentiated cell products, or inhibition of plant synthases. Thus, the phenotype of a particular plant may be modified.

A purified *R. communis* synthase is provided and used to obtain nucleic acid sequences. From the protein or the sequences other plant synthases may be obtained.

All publications and patent applications mentioned in this specification are indicative of the level of skill of those skilled in the art to which this invention pertains. All publications and patent applications are herein incorporated by referenced to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A cDNA sequence encoding a *Ricinus communis* β-ketoacyl-ACP synthase protein, wherein said cDNA sequence comprises the mature protein encoding portion of said synthase protein, and wherein said mature protein has a molecular weight of approximately 50 kD.

2. A cDNA sequence encoding a *Ricinus communis* β-ketoacyl-ACP synthase protein, wherein said cDNA sequence comprises the mature protein encoding portion of said synthase protein, and wherein said mature protein has a molecular weight of approximately 46 kD.

3. A DNA construct comprising, as operably joined components, in the 5' to 3' direction of transcription, a transcription initiation region functional in a host cell, a translation initiation region functional in a host cell, said β-ketoacyl-ACP synthase protein encoding sequence of claim 1 or claim 2, and a transcriptional termination region functional in a host cell, wherein said synthase protein encoding sequence is oriented for expression of sense sequence, and wherein at least one of said initiation or termination regions is heterologous to said synthase protein encoding sequence.

4. The DNA construct of claim 3 wherein said initiation and termination regions are functional in a plant cell, and wherein said construct further comprises, immediately 5' to said mature synthase protein encoding sequence, a transit peptide encoding sequence.

5. The construct of claim 3 wherein said host is *E. coli.*

6. The DNA construct of claim 4 wherein said transcription initiation region is from a gene preferentially expressed in seed tissue.

7. A DNA construct comprising, in the 5' to 3' direction of transcription, a transcription initiation region functional in a plant seed cell, said β-ketoacyl-ACP synthase protein encoding sequence of claim 1 or claim 2 and a transcriptional termination region functional in a plant seed cell, wherein said β-ketoacyl-ACP synthase protein encoding sequence is oriented for expression of antisense sequence.

8. The DNA construct of claim 4 wherein said transit peptide encoding sequence is naturally associated with said β-ketoacyl-ACP synthase encoding sequence.

9. The DNA construct of claim 7 wherein said transcription initiation region is from a gene preferentially expressed in seed tissue.

10. A plant cell comprising a DNA construct according to claim 6.

11. A plant cell comprising a recombinant DNA construct said construct comprising in the 5' to 3' direction of transcription, a transcription initiation region functional in a plant cell, a translation initiation region functional in a plant cell, said protein encoding sequence of claim 1 or claim 2, and a transcriptional termination region functional in a plant cell, wherein said plant encoding sequence is heterologous to said plant cell and wherein said plant cell further comprises a heterologous marker for detection of transformed cells comprising said construct.

12. The plant cell of claim 11 wherein said plant β-ketoacyl-ACP synthase protein encoding sequence is heterologous to said plant cell.

13. A plant or plant part comprised of cells having integrated into the genome of said cells a DNA construct according to claim 6.

14. A plant cell comprising a DNA construct according claim 4.

15. A plant or plant part comprised of cells having integrated into the genome of said cells a DNA construct according claim 4.

* * * * *